US008658762B2

(12) United States Patent
Liu

(10) Patent No.: US 8,658,762 B2
(45) Date of Patent: Feb. 25, 2014

(54) POLYPEPTIDES THAT INHIBIT DOPAMINE D2 RECEPTOR-DISC1 INTERACTION AND METHODS OF USE THEREOF

(75) Inventor: Fang Liu, Toronto (CA)

(73) Assignee: Centre for Addiction and Mental Health, Toronto, Ontario (CA)

( * ) Notice: Subject to any disclaimer, the term of this patent is extended or adjusted under 35 U.S.C. 154(b) by 0 days.

(21) Appl. No.: 13/263,702

(22) PCT Filed: Apr. 9, 2010

(86) PCT No.: PCT/CA2010/000535
§ 371 (c)(1),
(2), (4) Date: Dec. 13, 2011

(87) PCT Pub. No.: WO2010/115286
PCT Pub. Date: Oct. 14, 2010

(65) Prior Publication Data
US 2012/0093822 A1    Apr. 19, 2012

Related U.S. Application Data

(60) Provisional application No. 61/168,128, filed on Apr. 9, 2009.

(51) Int. Cl.
| *A61K 38/00* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *G01N 33/53* | (2006.01) |
| *G01N 33/567* | (2006.01) |
| *G01N 33/566* | (2006.01) |
| *C12Q 1/02* | (2006.01) |

(52) U.S. Cl.
USPC ............ 530/326; 530/327; 530/328; 435/7.1; 435/7.2; 435/29; 436/501

(58) Field of Classification Search
None
See application file for complete search history.

(56) References Cited

U.S. PATENT DOCUMENTS

| 2002/0065405 | A1* | 5/2002 | Padigaru et al. ............. 536/23.1 |
| 2002/0086362 | A1* | 7/2002 | Li et al. ......................... 435/69.1 |
| 2008/0234183 | A1 | 9/2008 | Hallbrink et al. |
| 2009/0111733 | A1* | 4/2009 | Park et al. ......................... 514/2 |
| 2011/0027293 | A1* | 2/2011 | Munawar ..................... 424/159.1 |
| 2012/0134991 | A1* | 5/2012 | Liu ............................. 424/134.1 |

FOREIGN PATENT DOCUMENTS

| WO | WO 2006/116874 A1 | 11/2006 |
| WO | WO 2008/021290 | 2/2008 |
| WO | WO 2009/149560 A1 | 12/2009 |
| WO | WO 2009/154697 A2 | 12/2009 |

OTHER PUBLICATIONS

Accila D, et al. PNAS 93:1945-1949, Mar. 1996.*
International Search Report, PCT/CA2010/000535, Jun. 22, 2010, pp. 1-6.
Liisa Tomppo et al., "Association Between Genes of Disrupted in Schizophrenia 1 (DISC1) Interactors and Schizophrenia Supports the Role of the DISC1 Pathway in the Etiology of Major Mental Illnesses," *Biol. Psychiatry*, Jun. 15, 2009, 65 (12): pp. 1055-1062.
Nicholas J. Brandon et al., "Understanding the Role of DISC1 in Psychiatric Disease and during Normal Development," *The Journal of Neuroscience*, Oct. 14, 2009, 29(41): pp. 12768-12775.
Robin M. Murray et al., "Schizophrenia: From developmental deviance to dopamine dysregulation," *European Neuropsychopharmacology*, 2008, 18: pp. S129-S134.
Seeman, P., et al., "Antipsychotic Drugs: Direct Correlation between Clinical Potency and Presynaptic Action on Dopamine Neurons," *Science, New Series*, vol. 188, No. 4194, Jun. 20, 1975, pp. 1217-1219.
Creese, Ian, et al., "Dopamine Receptor Binding Predicts Clinical and Pharmacological Potencies of Antischizophrenic Drugs," *Science, New Series*, vol. 192, No. 4238, Apr. 30, 1976, pp. 481-483.
Seeman, P., et al, "Antipsychotic drug doses and neuroleptie/dopamine receptors," *Nature* vol. 26, Jun. 24,1976, pp. 717-719.
Crow, T. J., at al, "Abnormal involuntary Movements in Schizophrenia: Are They Related to the Disease Process or Its Treatment? Are They Associated with Changes in Dopamine Receptors?," *Journal of Clinical Psychopharmacology* vol. 2, No. 5, Oct. 1982, pp. 336-340.
Mita, T., at al., "Decreased Serotonin $S_2$ and Increased Dopamine $D_2$ Receptors in Chronic Schizophrenics," *Biol. Psychiatry*, vol. 21, 1986, pp. 1407-1414.
Wong, D. F., at al, "Positron Emission Tomography Reveals Elevated D\$_{2}\$ Dopamine Receptors in Drug-Naive Schizophrenics," *Science, New Series*, vol. 234, No. 4783, Dec. 29, 1986, pp. 1558-1563.
Lieberman, J.A., et al., "Provocative tests with psychostimulant drugs in schizophrenia," *Psychopharmacology*, vol. 91, 1987, pp. 415-433.
Mansbach, Robert S., et al., "Dopaminergic stimulation distupts sensorimotor gating in the rat," *Psychpharmacology*, vol. 94, 1988, pp. 507-514.

(Continued)

*Primary Examiner* — Robert Landsman
(74) *Attorney, Agent, or Firm* — Haynes and Boone, LLP

(57) ABSTRACT

The present invention provides compounds, compositions and methods for inhibiting D2R-DISC1 interaction. Specifically, the present invention provides a polypeptide comprising the amino acid sequence KIYIVLRRRRKRVNT (SEQ ID NO: 1) or SEQ ID NO:5, a fragment thereof, or a polypeptide comprising an amino acid sequence that is at least 80% identical to SEQ ID NO: 1 or 5, or a fragment thereof, wherein the polypeptide is not a naturally occurring dopamine receptor. Also provided is a method of identifying an agent that inhibits the interaction of D2R with DISC1, a method of identifying an agent that binds to the polypeptide sequence defined by SEQ ID NO: 1 or 5, and a method of inhibiting D2R interaction with DISC1 in a mammal comprising administering an agent that inhibits the interaction of D2R with DISC1 to the mammal.

14 Claims, 8 Drawing Sheets

(56) References Cited

OTHER PUBLICATIONS

Murray, C. J. L., et al., "The Global Burden of Disease in 1990," *Harvard University Press, Boston*, pp. 261-267.

Montmayeur, J.P., et al., "Differential expression of the mouse $D_2$ dopamine receptor isoforms," *FEBS Letters*, vol. 278, No. 2, Jan. 1991.

Okamoto, T., et al., "Identification of a Gs Activator Region of the β2-Adrenergic Receptor That Is Autoregulated via Protein Kinase A-Dependent Phosphorylation," *Cell* No. 67, Nov. 15, 1991, pp. 723-730.

Van Tol, Hubert H.M., et al., "Multiple dopamine D4 receptor variants in the human population," *NATURE*, vol. 358, Jul. 9, 1992, pp. 149-152.

Lichter, Jay B., et al., A hypervariable segment in the human dopamine receptor $D_4$ (DRD4) gene, *Human Molecular Genetics*, vol. 2, No. 6, 1993, pp. 767-773.

Liu, Yun, et al., "Modulation of dopamine $D_3$ receptor binding by N-ethylmaleimide and neurotensin," *Brain Research 643*, 1994, pp. 343-348.

Seeman, Philip, et al., "Dopamine receptor pharmacology," *Tips*, vol. 15, Jul. 1994, pp. 264-270.

Iversen, S. D., "Interactions between excitatory amino acids and dopamine systems in the forebrain: implications for schizophrenia and Parkinson's disease," *Behavioural Pharmacology*, No. 6, 1995, pp. 478-491.

Livak, Kenneth J., et al., "Variability of dopamine D4 receptor (DRD4) gene sequence within and among nonhuman primate species," *Proc. Natl. Acad. Sic. USA*, vol. 92, Jan. 1995, pp. 427-431.

Cross, Darren A.E., et al., "Inhibition of glycogen synthase kinase-3 by insulin mediated by protein kinase B," *Nature*, vol. 378, No. 21/28, Dec. 1995, p. 785-789.

Seeman, Philip, et al., "Dopamine and Serotonim Receptors. Amino Acid Sequences, and Clinical Role in Neuroleptic Parkinsonism," *Jpn. J Pharmacol*. 71, 1996, pp. 187-204.

Schmauss, Claudia, Enhanced Cleavage of an Atypical Intro of Dopamine $D_3$ Receptor Pre-mRNA in Chronic Schizophrenia, *The Journal of Neuroscience*, Dec. 15, 1996, 16(24): 7902-7909.

Accili, Domenico, et al., "A targeted mutation of the D3 dopamine receptor gene is associated with hyperactivity in mice," *Proc. Natl. Acad. Sci. USA*, vol. 93, Mar. 1996, pp. 1945-1949.

Hagan, J.J., et al., "Parkinson's disease: prospects for improved drug therapy," *Tips*, vol. 18, May 1997, pp. 156-163.

Wong, Dean F., et al., "Quantification of Neuroreceptors in the Living Human Brian: III. $D_2$ Like Dopamine Receptors: Theory, Validation, and Changes During Norman Aging," *Journal of Cerebral Blood Flow and Metabolism*, vol. 17, No. 3, 1997, pp. 316-330.

Sanyal, S., et al., "Dopamine D4 Receptor-Mediated Inhibition of Cyclic Adenosine 3', 5'-Monophosphate Production Does Not Affect Prolactin Regulation," *Endocrinology*, vol. 138, No. 5, 1997, pp. 1871-1878.

Wong, Dean F., et al., "Quantification of Neuroreceptors in the Living Human Brian: IV. Effect of Aging and Elevations of $D_2$ Like Receptors in Schizophrenia and Bipolar Illness," *Journal of Cerebral Blood Flow and Metabolism*, vol. 17, No. 3, 1997, pp. 331-342.

Watanabe, Masataka, et al., "Increase of Extracellular Dopamine in Primate Prefrontal Cortex During a Working Memory Task, "*J Neurophysiol* No. 78, 1997, pp. 2795-2798.

Schultz, Wolfram, "Dopamine neurons and their role in reward mechanisms," *Neurobiology*, No. 7, 1997, pp. 191-197.

Picetti, Roberto, et al., "Dopamine D2 Receptors in Signal Transduction and Behavior," *Critical Reviews™ in Neurobiology*, 11(2&3), 1997, pp. 121-142.

Shupliakov, Oleg, et al., "Synaptic Vesicle Endocytosis Impaired by Disruption of Dynamin-SH3 Domain Interactions," *Science, New Series*, vol. 276, No. 5310, Apr. 1997, pp. 259-263.

Beninger, Richard J., et al., "Dopamine D1-like Receptors and Reward-related Incentive Learning," *Neuroscience & Biobehavioral Review*, vol. 22, No. 2, 1998, pp. 335-345.

Hollerman, Jeffrey R., et al., "Influence of Reward Expectation on Behavior-Related Neuronal Activity in Primate Striatum," *J. Neurophysiol*, 1998:80, pp. 947-963.

Caron, Marc G., et al., "Dopamine receptors: from structure to function," *Physiological Reviews*, No. 78.1, Jan. 1998, p. 189.

Hebert, Terrence E., et al., "Functional rescue of a constitutively desensitized $β_2$AR through receptor dimerization," *Biochem. J.*, vol. 330, 1998, pp. 287-293.

Khan, Zafar U., et al., "Prominence of the dopamine $D_2$ short isoform in dopaminergic pathways," *Proc. Natl. Acad. Sci. USA*, vol. 95, Jun. 1998, pp. 7731-7736.

Smith, F. Donelson, et al., "Cell Biology and Metabolism: Association of the D2 Dopamine Receptor Third Cytoplasmic Loop with Spinophilin, a Protein Phosphatase-l-interacting Protein," *J. Biol. Chem.*, 274, 1999, pp. 19894-19900.

Schwarze, Steven R., et al., "In vivo Protein Transduction: Delivery of a Biologically Active Protein into the Mouse," *Science*, No. 285, Sep. 3, 1999, pp. 1569-1572.

Millar, J. Kirsty, et al., "Disruption of two novel genes by a translocation co-segregating with schizophrenia," *Human Molecular Genetics*, vol. 9, No. 9, 2000, pp. 1415-1423.

Rocheville, Magalie, et al., "Receptors for Dopamine and Somatostatin: Formation of Hetero-Oligomers with Enhanced Functional Activity," *Science, New Series*, vol. 288, No. 5463, Apr. 7, 2000, pp. 154-157.

Usiello, Alessandro, et al., "Distinct functions of the two isoforms of dopamine D2 receptors," *Nature*, vol. 408, Nov. 9, 2000, pp. 199-203.

Li, M et al "Modulation of Dopamine $D_2$ Receptor Signaling by Actin-Binding Protein (ABP-280)," *Mol. Pharmacol.*, vol. 57, 2000, pp. 446-452.

Bofill-Cardona, Elisa, et al., "Mechanisms of Signal Transduction: Binding of Calmodulin to the D2-Dopamine Receptor Reduces Receptor Signaling by Arresting the G Protein Activation Switch," *J. Biol. Chem.*, No. 275, 2000, pp. 32672-32680.

Wang, Yanya, et al., Dopamine D2 Long Receptor-Deficient Mice Display Alterations in Striatum-Dependent Functions, *J. Neuroscience*, Nov. 15, 2000, pp. 8305-8314.

Seeman, Philip, et al., "Schizophrenia: More dopamine, more $D_2$ receptors," *PNAS*, vol. 97, No. 14, Jul. 5, 2000, pp. 7673-7675.

Liu, Fang, et al., "Direct protein-protein coupling enables cross-talk between dopamine D5 and 'Y'-Aminobutyric acid a receptors," *Nature*, vol. 403, Jan. 20, 2000, pp. 274-279.

Abi-Dargham, Anissa, et al., "Increased baseline occupancy of D2 receptors by dopamine in schizophrenia," *PNAS*, vol. 97, No. 14, Jul. 5, 2000, pp. 8104-8109.

Futaki, Shiroh, et al., "Arginine-rich peptides: An abundant source of membrane-permeable peptides having potential as carriers for intracellular protein delivery," *The Journal of Biological Chemistry*, vol. 276, No. 8, Nov. 2000, p. 5836, XP002210171.

Tallerico, Teresa et al., "Schizophrenia: elevated mRNA for dopamine $D2_{Longer}$ receptors in frontal cortex," *Molecular Brain Research*, vol. 87, 2001, pp. 160-165.

Geyer, Mark A. et al., "Pharmacological studies of prepulse inhibition models of sensorimotor gating deficits in schizophrenia: a decade in review," *Psychopharmacology*, No. 156, 2001, pp. 117-154.

Greengrad, Paul, "The Neurobiology of Slow Synaptic Transmission," *Science, New Series*, vol. 294, No. 5544, Nov. 2, 2001), pp. 1024-1030.

Lee, Frank J.S., et al., "Direct binding and functional coupling of a-synuclein to the dopamine transporters accelerate dopamine-induced apoptosis," *FASEB J.*, No. vol. 15, Apr. 2001, pp. 916-926.

Lin, Ridwan, et al., "Dopamine D2 and D3 receptors are linked to the actin cytoskeleton via interaction with filamin a," *PNAS*, vol. 98, No. 9, Apr. 24, 2001, pp. 5258-5263.

Blackwood, D.H.R., et al., "Schizophrenia and Affective Disorders—Cosegregation with a Translocation at Chromosome 1q42 That Directly Disrupts Brain-Expressed Genes: Clinical and P300 Findings in a Family," *Am. J. Hum. Genet.*, No. 69, 2001, pp. 428-433.

(56) References Cited

OTHER PUBLICATIONS

Scarselli, Marco, et al., "Mechanisms of Signal Transduction: D2/D3 Dopamine Receptor Heterodimers Exhibit Unique Functional Properties," *The Journal of Biological Chemistry*, vol. 276, No. 32, Aug. 10, 2001, pp. 30308-30314.

McCullumsmith, Robert E., et al., "Striatal Excitatory Amino Acid Transporter Transcript Expression in Schizophrenia, Bipolar Disorder, and Major Depressive Dirorder," *Neuropsychopharmacology*, vol. 26, No. 3, 2002, pp. 368-375.

Centonze, Diego, et al., "Dopamine D2 Recepto-Mediated Inhibition of Dopaminergic Neurons in Mice Lacking D2L Receptors," *Neuropsychopharmacology*, vol. 27, No. 5, 2002, pp. 723-726.

Hillion, Joelle, et al., "Mechanisms of Signal Transduction: Coaggregation, Cointernalization, and Codesensitization of Adenosine A2A Receptors and Dopamine D2Receptors," *J Biol. Chem.*, vol. 277, No. 20, Feb. 28, 2002, pp. 18091-18097.

Kabbani, Nadine et al., "Interaction with neuronal Calcium Sensor NCS-1 Mediates Desensitization of the D2 Dopamine Receptor," *J. Neurosci*, vol. 22, No. 19, Oct. 1, 2002, pp. 8476-8486.

Aarts, Michelle, et al., "Treatment of ischemic brain damage by perturbing NMDA receptor- PSD-95 protein interactions," *Science, New Series*, vol. 298, No. 5594, Oct. 25, 2002, pp. 846-850.

Lavine, Natalie, et al., "Mechanisms of Signal Transduction: G Protein-coupled Receptors Form Stable Complexes with Inwardly Rectifying Potassium Channels and Adenylyl Cyclase," *J. Biol. Chem.*, vol. 277, No. 48, 2002, pp. 46010-46019.

Binda, Alicia V., et al., "D2 and D3 Dopamine Receptor Cell Surface Localization Mediated by Interaction with Protein 4.1N," *Mol. Pharmacol.* vol. 62, No. 3, 2002, pp. 507-513.

Lee, F. J., et al., "Dual Regulation of NMDA Receptor Functions by Direct Protein-Protein Interactions with the Dopamine D1 Receptor," *Cell*, vol. 111, Oct. 18, 2002, pp. 219-230.

Ma, L., et al., "Cloning and Characterization of DISC1, the Mouse Ortholog of DISC1 (Disrupted-in-Schizophrenia 1)," *Genomics*, vol. 80 No. 6, Dec. 2002, pp. 662 -672.

Hwu, H. G., et al., "Linkage of schizophrenia with chromosome 1q loci in Taiwanese families," Mol. Psychiatry, vol. 8, 2003, pp. 445-452.

Griffon, N., et al., "CLIC6, a member of the intracellular chloride channel family, interacts with dopamine D2-like receptors," *Mol. Brain Res.* vol. 117, 2003, pp. 47-57.

Morris, J. A. et al., "DISC1 (Disrupted-In-Schizophrenia 1) is a centrosome-associated protein that interacts with MAP1A, MIPT3, ATF4/5 and NUDEL: regulation and loss of interaction with mutation," Hum. Mol. Genet, vol. 12, No. 13, 2003, pp. 1591-1608.

Kapur, Shitij, et al., "Antipsychotic Dosing in Preclinical Models Is Often Unrepresentative of the Clinical Condition: A Suggested Solution Based on in Vivo Occupancy," *J. Pharmacol Exp Ther.*, vol. 305, No. 2, 2003, pp. 625-631, 919.

Kapur, Shitij, et al., "Correction to Antipsychotic dosing in preclinical models is often unrepresentative of the clinical condition: a suggested solution based on in vivo occupancy," *J. Pharmacol. Exp. Ther.* 305, 2003, p. 919.

Taylor, M. S et al., "Evolutionary constraints on the Disrupted in Schizophrenia locus," *Genomics*, vol. 81, 2003, pp. 67-77.

Hennah, W., et al., "Haplotype transmission analysis provides evidence of association for DISC1 to schizophrenia and suggests sex-dependent effects," *Hum. Mol. Gene.t*, vol. 12, No. 23, 2003, pp. 3151-3159.

Takeuchi, Y., et al., "Differential subcellular localization of two dopamine $D_2$ receptor isoforms in transfected NG108-15 cells," *J. Neurochem.*, vol. 85, 2003, pp. 1064-1074.

Bergson, C., et al., "Dopamine receptor-interacting proteins: the $Ca^{2+}$ connection in dopamine signaling," *Trends Pharmaco.l Sci.*, vol. 24, No. 9, 2003, pp. 486-492.

Lindgren, N., et al., "Distinct roles of dopamine D2L and D2S receptor isoforms in the regulation of protein phosphorylation at presynaptic and postsynaptic sites," *PNAS*, vol. 100, No. 7, Apr. 1, 2003, pp. 4305-4309.

Macey, T. A., et al., "Preferential Interaction between the dopamine D2 receptor and Arresting in Neostriatal Neurons," *Mol. Pharmacol.*, vol. 66, No. 6, 2004, pp. 1635-1642.

Gould, T. D., et al., "AR-A014418, a selective GSK-3 inhibitor, produces antidepressant-like effects in the forced swim test," *Int. J. Neuropsychopharmacol.*, vol. 7, 2004, pp. 387-390.

Gabriele, J.P., et al., "Decreased expression of a 40-kDa catecholamine-regulated protein in the ventral striatum of schizophrenic brain specimens from the Stanley Foundation Neuropathology Consortium," *Schizophr. Res.*, 74, 2005, pp. 111-119.

Ekelund, J., et al., "Replication of 1q42 linkage in Finnish schizophrenia pedigrees," *Mol. Psychiatry*, No. 9, 2004, pp. 1037-1041.

Emamian, E S , et al., "Convergent evidence for impaired AKT1-GSK3β signaling in schizophrenia," *Nat. Genet.*, vol. 36, No. 2, Feb. 2004, pp. 131-137.

Beaulieu, J. M., et al., "Lithium antagonizes dopamine-dependent behaviors mediated by an AKT/glycogen synthase kinase 3 signaling cascade," *Proc Natl Acad Sci USA*, vol. 101, No. 14, Apr. 6, 2004, pp. 5099-5104.

Kockelkorn, Thessa T. J.P.., et al., "Association study of polymorphisms in the 5' upstream region of human DISC1 gene with schizophrenia," *Neurosci. Lett.*, 368, 2004, pp. 41-45.

Hodgkinson, C. A., et al., "Disrupted in Schizophrenia 1 (DISC1): Association with Schizophrenia, Schizoaffective Disorder, and Bipolar Disorder," *Am. J Hum. Genet.*, No. 75, 2004, pp. 862-872.

Goeree, R., et al., "The economic burden of schizophrenia in Canada in 2004" *Curr. Med. Res. Opin.*, vol. 12, No. 12, 2005, pp. 2017-2028.

Sachs, N. A., et al., "A frameshift mutation in Disrupted in Schizophrenia 1 in an American family with schizophrenia and schizoaffective disorder," *Mol. Psychiatry*, No. 10, 2005, pp. 758-764.

O'Dowd, B. F., et al., "Protein Structure and Folding: Dopamine Receptor Oligomerization Visualized in Living Cells," *J. Biol. Chem.*, 280, 2005, pp. 37225-37235.

Ralph, R. J., et al., "Dopamine D1 and D2 Agonist Efects on Prepulse Inhibition and Locomotion: Comparison of Sprague-Dawley Rats to Swiss-Webster, 129X1/SvJ, C57BL/6J, and Dba/2J Mice," *J. Pharmacol. Exp. Ther.*, vol. 312, No. 2, 2005, pp. 733-741.

Kearn, C.S., et al, "Concurrent Stimulation of Cannabinoid CB1 and Dopamine D2 Receptors Enhances Heterodimer Formation: A Mechanism for Receptor Cross-Talk?," Mol. Pharmacology, vol. 67, No. 5, 2005, pp. 1697-1704.

Hamshere, M. L., et al., "Genomewide Linkage Scan in Schizoaffective Disorder: Significant Evidence for Linkage at 1q42 close to DISC1, and Suggestive Evidence at 22q11 and 19p13," *Arch. Gen. Psychiatry*, vol. 62, Oct. 2005, pp. 1081-1088.

Miyamoto, S., et al., "Treatments for schizophrenia: a critical review of pharmacology and mechanisms of action of antipsychotic drugs," *Mol. Psychiatry*, vol. 10, 2005, pp. 79-104.

Tassabehji, May, et al., "GTF2IRD1 in Craniofacial Development of Humas and Mice," *Science, New Series*, vol. 310, No. 5751, Nov. 18, 2005, pp. 1184-1187.

Alimohamad, H., et al., "Antipsychotics Alter the Protein Expression Levels of β-Catenin and GSK-3 in the Rat Medial Prefrontal Cortex and Striatum," *Biol. Psychiatry*, vol. 57, 2005, pp. 533-542.

Callicott, J.H., et al., Variation in DISC1 affects hippocampal structure and function and increases risk for Schizophrenia, *PNAS*, vol. 102, No. 24, 2005, pp. 8627-8632.

Binda, A. V., et al., "Regulation of dense core vesicle release from PC12 cells by interaction between the D2 dopamine receptor and calcium-dependent activator protein for secretion (CAPS)," Biochem. Pharmacol., 69, 2005, pp. 1451-1461.

Beaulieu, J. M., et al., "An Akt/β-Arrestin 2/PP2A Signaling Complex Mediates Dopaminergic Neurotransmission and Behavior," *Cell*, vol. 122, 2005, pp. 261-273.

Zou, S., et al., "Protein-Protein Coupling/Uncoupling Enables Dopamine $D_2$ Receptor Regulation of AMPA Receptor-Mediated Excitotoxicity," *J. Neurosci.*, vol. 25, No. 17, 2005, pp. 4385-4395.

Park, S. K., et al., "Par-4 Links Dopamine Signaling and Depression," *Cell*, vol. 122, Jul. 29, 2005, pp. 275-287.

Bartlett, S. E., et al., "Dopamine responsiveness is regulated by targeted sorting of D2 receptors," *PNAS*, vol. 102, Aug. 9, 2005, pp. 11521-11526.

(56) References Cited

OTHER PUBLICATIONS

Kamiya, A., et al., "A schizophrenia-associated mutation of DISC1 perturbs cerebral cortex development," *Nat. Cell. Bio.*, vol. 7, No. 12, Dec. 2005, pp. 1167-1178.

Insel, T. R., et al., "Cure therapeutics and strategic prevention: raising the bar for mental health research," *Mol. Psychiatry*, vol. 11, 2006, pp. 11-17.

Seeman, P., "Targeting the dopamine D2 receptor in schizophrenia," *Expert Opin. Ther. Targets*, 2006, 10 (4), pp. 515-531.

Ishizuka, K., et al., "A Review of Disrupted-In-Schizophrenia-1 (DISC1): Neurodevelopment, Cognition, and Mental Conditions," *Biol. Psychiatry*, vol. 59, 2006, pp. 1189-1197.

Porteous, D. J., et al., "The Genetics and Biology of Disc1—An Emerging Role in Psychosis and Cognition," *Biol. Psychiatry*, vol. 60, 2006, pp. 123-131.

Liu, X. Y., et al., "Modulation of D2R-NR2B Interactions in Response to Cocaine," *Neuron.* 52, 2006, pp. 897-909.

Beaulieu, J. M., et al., "Mechanisms of Signal Transduction: Paradoxical Striatal Cellular Signaling Responses to Psychostimulants in Hyperactive Mice," *J. Biol. Chem.* 281 (43), Oct. 27, 2006, pp. 32072-32080.

Koike, H., et al., "Disc1 is mutated in the 12956/SvEv strain and modulates working memory in mice," *Proc. Natl. Acad. Sci.*, vol. 103, No. 10, Mar. 7, 2006, pp. 3693-3697.

Clapcote, S. J., et al., "Behavioral phenotypes of Disci Missense Mutations in Mice," *Neuron.* 54, 2007, pp. 387-402.

Li, X., et al., "Regulation of mouse brain glycogen synthase kinase-3 by atypical antipsychotics," *Int. J. Neuropsychopharmacol* 10, 2007, pp. 7-19.

Pletnikov, M. V., et al., "PC12 cell model of inducible expression of mutant DISC1: New evidence for a dominant-negative mechanism of abnormal neuronal differentiation," *Neurosci. Res.* 58, 2007, pp. 234-244.

Hattori, T., et al., "A novel DISC1-interacting partner DISC1-Binding Zinc-finger protein: implication in the modulation of DISC1-dependent neurite outgrowth," *Mol. Psychiatry*, vol. 12, 2007, pp. 398-407.

Lee, F. J., et al., "Dopamine transporter cell surface localization facilitated by a direct interaction with the dopamine D2 receptor," *The EMBO Journal*, vol. 26, No. 8, 2007, pp. 2127-2136.

Li, W., et al., "Specific developmental disruption of disrupted-in-schizophrenia-1 function results in schizophrenia-related phenotypes in mice," *PNAS*, vol. 104., No. 46, Nov. 13, 2007, pp. 18280-18285.

Hikida, T., et al., "Dominant-negative DISC1 transgenic mice display schizophrenia-associated phenotypes detected by measures translatable to humans," *PNAS* 104, Sep. 14, 2007, pp. 14501-14506.

Free, R. B., et al., "Mechanisms of Signal Transduction: D1 and D2 Dopamine Receptor Expression Is Regulated by Direct Interaction with the Chaperone Protein Calnexin," *J. Biol. Chem.* vol. 282, 2007, pp. 21285-21300.

Beaulieu, J.M., et al., The Akt-GSK-3 signaling cascade in the actions of dopamine, *Trends Pharmacol. Sci.*, vol. 28, No. 4, 2007, pp. 166-172.

Patil, S. T., et al "Activation of mGlu2/3 receptors as a new approach to treat schizophrenia: a randomized Phase 2 clinical trial," *Nat. Med.*, vol. 13, No. 9, Sep. 2007, pp. 1102-1107.

Pletnikov, M. V., et al., "Inducible expression of mutant human DISC1 in mice is associated with brain and behavioral abnormalities reminiscent of schizophrenia," *Mol. Psychiatry*, vol. 13, 2008, pp. 173-186.

Beaulieu, J. M., et al., "A β-arrestin 2 Signaling Complex Mediates Lithium Action on Behavior," *Cell* 132, 2008, pp. 125-136.

Masri, B., et al., "Antagonism of dopamine D2 receptor/beta-arrestin 2 interaction is a common property of clinically effective antipsychotics," *PNAS*, vol. 105, No. 36, Sep. 9, 2008, pp. 13656-13661.

Beaulieu, J. M., et al., Akt/GSK3 Signaling in the Action of Psychotropic Drugs, *Annu. Rev. Pharmacol. Toxicol.* vol. 49, 2009, pp. 327-345.

EPO, Supplementary European Search Report, Feb. 1, 2013, 8 pages.

\* cited by examiner

A

B

C

POLYPEPTIDES THAT INHIBIT DOPAMINE D2 RECEPTOR-DISC1 INTERACTION AND METHODS OF USE THEREOF

CROSS-REFERENCE TO RELATED APPLICATION

This is the national stage of PCT/CA2010/000535, filed Apr. 9, 2010, which claims the benefit of U.S. Provisional Patent Application No. 61/168,128, filed Apr. 9, 2009, the contents of each of which is hereby incorporated herein in its entirety by express reference thereto.

FIELD OF INVENTION

The present invention relates to compositions and methods for modulating D2R-DISC1 interaction.

BACKGROUND OF THE INVENTION

Dopamine (DA), acting through D1-like and D2-like receptors, has a major role in regulating neuronal motor control, cognition, event prediction and emotion (5-10). In mammals, five distinct genes, termed D1/D5 for D1-like receptors and D2/D3/D4 for D2-like receptors, encode DA receptors. These receptors belong to a super-family of single polypeptide 7-transmembrane domain receptors that exert their biological effects via intracellular G-protein coupled signalling cascades (11). D1 and D5 receptors preferentially couple to Gs proteins, stimulating the activity of adenylate cyclase and PKA dependent pathways. Dopamine D2 receptors (D2R) display a more complex pattern of signal transduction primarily due to their coupling to subtype-specific members of the Gi/Go protein family (11). D2R are known to stimulate a number of signal transduction pathways including the inhibition of adenylate cyclase activity, PI turnover, potentiation of arachidonic acid release, inwardly rectifying K+ and Ca2+ channels and mitogen activated protein kinases (12). D1- and D2-like receptors are further differentiated on pharmacological grounds with D1-like receptors selectively binding agonists [e.g. fenoldopam, SKF-81297] and antagonists [SCH-23390] of the benzazepine and benzonapthazine class with high affinity, while D2-like receptors bind selectively to wide variety of agonists and antagonists from numerous structural classes, including aminotetralins, butyrophenones and substituted benzamides. Furthermore, as opposed to the D1/D5 receptor genes that are intron-less, the molecular diversity and multiplicity of the D2-like receptor subfamily arises from alternative splicing of the D2R, termed D2Long (D2L) and D2Short (D2S) (12); abnormally spliced truncated variants of the D3 receptor (13-14) and numerous polymorphic variants of D4 receptors (15) as well as 19 additional allelic variants found in humans (16-17). The molecular isoforms of the D2R are identical except for the presence of a 29 amino acid insert in D2L while polymorphic D4 receptors differ in both the number and order of a 48 base-pair repeat sequence. These insertions/variations occur within the third cytoplasmic loop of D2/D4, a domain thought to encode sequence motifs enabling receptor coupling to specific G-proteins (18-19). In addition, several studies suggest that the D2S splice variant is predominantly found on pre-synaptic terminals while the D2L is mostly found post-synaptically (20-25).

As described above, D2R has been shown to regulate cAMP-PKA and Ca2+ pathways through Gi/o-dependent signaling (11, 26). However, recent studies have suggested that D2R activate the Akt/GSK-3 pathway via G protein-independent (β-arrestin 2-dependent) signaling (27, 28, 101-104). D2R-mediated Akt/GSK-3 regulation involves the recruitment of β-arrestin 2 to the D2R and the formation of signalling complexes containing β-arrestin 2, PP2A (protein phosphatase 2A), and Akt, which leads to specific dephosphorylation/inactivation of the serine/threonine kinase Akt on its regulatory Thr308 residue but not the second regulatory residue (Ser473) (28), Dephosphorylation of Akt in response to DA leads to a reduction of kinase activity and a concomitant activation of its substrates GSK-3α/β since both are negatively regulated by Akt (28-29). Functionally, pharmacological activation of Akt or inhibition of GSK3α/β results in reduction of DA-associated locomotor activity in both DAT-Knock-out mice and wild-type mice treated with amphetamine (28,30). Moreover, mice lacking one allele of the GSK-3β gene show markedly reduced locomotor responses to amphetamine (28), while mice lacking the Akt isoform Akt1 display behavioural manifestations generally associated with enhanced dopaminergic responses (31), thus supporting a role for the Akt/GSK3 signalling pathway in the expression of DA-associated behaviours. β-arrestin 2 deficiency in mice results in reduction of dopamine-dependent behaviours, loss of Akt regulation by DA in the striatum, and disruption of the DA-dependent interaction of Akt with its negative regulator, PP2A-indicating an important role for β-arrestin 2 in this process (27-28,32). Importantly, antipsychotics including haloperidol, clozapine, aripiprazole, chlorpromazine, quetiapine, olanzapine, risperidone, and ziprasidone all potently antagonize recruitment of β-arrestin 2 to D2R induced by activation of D2R (33-34). Lithium—a drug prescribed for the primary treatment of bipolar disorder, and used to augment treatment for schizophrenia and depression—regulates Akt/GSK3 signalling and related behaviours in mice by disrupting a signalling complex composed of Akt, β-arrestin 2, and PP2A (28,101). These data support an important role of D2R-mediated Akt/GSK-3 signalling in the pathology of mental illnesses.

Many studies demonstrate that D2R are involved in schizophrenia and antipsychotic medication action. First, there is a positive correlation between the clinical potency and D2R binding affinity of antipsychotic drugs (35-37). Second, there are increased levels of brain D2R in patients with schizophrenia as shown in post-mortem, PET and SPECT studies (38-44). Third, there are elevated D2R mRNA levels in the post-mortem frontal cortex of schizophrenia patients (45). Clinically, all current antipsychotics exert their effect through D2R3, and currently, there are no antipsychotics with a novel mechanism of action (46). The only new possibly different antipsychotic is the glutamate agonist LY404,039, which has been significantly effective in 100 Russian patients with schizophrenia (47).

In recent years, it has become evident that the diverse cellular properties of D2R can be regulated through their interaction with a class of molecules collectively termed DA receptor interacting proteins (DRIPs). DRIPs not only regulate receptor signalling, but contribute to receptor trafficking and stability. Proteins that interact with D2R include neurotransmitter receptors, transporters, ion channels, intracellular signalling proteins, cytoskeleton proteins, protein kinases and adaptor/chaperone proteins (48-67). Given that each specific protein-protein interaction enables the D2R to perform a specific function, the identification of D2R-interacting proteins may improve knowledge about the etiology of neuropsychiatric diseases and to develop treatments targeted at the underlying pathophysiology.

Disrupted-in-schizophrenia-1 (DISC1) was originally identified as a susceptibility gene for schizophrenia in a Scottish family carrying a balanced chromosomal translocation (1q42.1:11q14.3) that co-segregates with major mental illnesses including schizophrenia, bipolar disorder and major depression (LOD score 7.1) (68-70). Translocation carriers also showed a significant reduction in the P300 event-related potential-a general biomarker in schizophrenic patients (69). Genetic studies demonstrate significant linkage between the DISC1 locus and psychiatric illness in Finnish (71), Taiwanese (72) and Icelandic populations (73). Genetic association studies also support that DISC1 variants affect susceptibility to psychiatric disease (74-77). However, as with most complex disease phenotypes, some studies have not replicated these results, such as one with subjects of Japanese background (78).

DISC1 is comprised of 13 exons and encodes a protein of 854 amino acids that is conserved across primates and rodents, but shows little homology to other proteins and species (68, 79-80). Much remains unknown about DISC1 function, but the amino acid sequence suggests that it is likely to act as a scaffolding protein with multiple to binding motifs (81). The globular N-terminus contains nuclear localization signals. The coiled-coil C-terminus consists of different domains that allows DISC1 protein to interact with a variety of functionally diverse proteins in the brain, including: (a) microtubule-associated, centrosomal proteins including NudE-like (NUDEL), kendrin, microtubule-interacting protein associated with TRAF3 (MIPT3), and microtubule-associated protein 1A (MAP1A); (b) possible nuclear proteins such as activating transcription factor 4/5 (ATF4/5); (c) actin-associated proteins including spectrin and fasciculation and elongation protein zeta-1 (FEZ1); and (d) postsynaptic density-associated proteins that function in synaptic morphology and plasticity, such as Citron (82). Recently, phosphodiesterase 4B (PDE4B) was reported to bind to the NT of DISC1 (83). This interaction is predicted to play a regulatory role in cAMP signaling (80). The translocation results in a CT truncation of the DISC1 protein and thus affects its ability to form protein complexes and mediate downstream signals. Biochemical studies have indicated that DISC1 protein contains a self-interacting domain that allows the formation of a dimer. The truncated protein is thought to form a dimer with the wild-type protein, hence disturbing its normal function and subcellular distribution (84-85). This dominant-negative hypothesis was further supported by similar cellular effects observed with both the introduction of the CT-truncated mutant and suppression of endogenous DISC1 with RNA interference (84).

There are several types of genetic mouse models for DISC1, beginning with a spontaneous deletion variant in the DISC1 gene specific to the 129S6/SvEv strain (86). This mutation displays impaired working memory, which is consistent with the cognitive impairment in schizophrenia (86). Hikida et al. generated mice expressing a CT truncated DISC1 thought to act in a dominant negative fashion (DN-DISC1) and found significant anatomical (enlargement of lateral ventricles) and behavioural abnormalities (hyperactivity, disturbance in prepulse inhibition and depression-like deficits) (87). Interestingly, transgenic mice expressing only the DISC1 CT fragment (DISC1-cc) also resulted in schizophrenia-related phenotypes (88). Finally, Pletnikov's group derived transgenic mice with predominant expression of mutant human DISC1 (107). Overlapping anatomical and behavioural deficits such as enlarged lateral ventricles, neurite outgrowth defects, hyperactivity and abnormal spatial learning and memory functions were observed with this transgenic mouse line (89).

Two other independent mouse lines with DISC1 amino acid changes Q31L (127A/T) and L100P (334T/C)90 demonstrated both anatomical and behavioural changes consistent with those seen in schizophrenia: enlarged lateral ventricles on MRI, abnormal sensory gating measured with prepulse inhibition (PPI), deficits in anxiety-related exploratory behaviour and decreased social interaction. These abnormalities responded to the appropriate drug treatment used to target the same domains of dysfunction in humans. Each of the two mutant lines have overlapping but different types of behavioural deficits and pharmacological responses; the Q31L line has more depression-related symptoms whereas the L100P shows more psychosis-related symptoms (90). This is intriguing given the observation that the Scottish family members with the 1:11 translocation all shared the same breakpoint, but had a spectrum of clinical syndromes (68). These data point to new pathophysiological mechanisms involving dysfunction of DISC1 and GSK-3, and provide a link to the well-established DA hypothesis in schizophrenia.

There is a need in the art to identify novel therapeutic targets for treating schizophrenia and other medical conditions involving aberrant dopamine signalling and regulation. Further, there is a need in the art to identify new therapeutic agents for treating schizophrenia and other medical conditions involving aberrant dopamine signaling and regulation. There is also a need in the art for novel assays to identify such therapeutic agents.

SUMMARY OF THE INVENTION

The present invention relates to compositions and methods for modulating D2R-DISC1 interaction.

According to the present invention there is provided a polypeptide comprising the amino acid sequence KIYIVLR-RRRKRVNT (SEQ ID NO:1), a fragment thereof, or a polypeptide comprising an amino acid sequence that is at least 80% identical to SEQ ID NO:1, or a fragment thereof, wherein the polypeptide is not a naturally occurring dopamine receptor.

The present invention also provides a polypeptide as described above further comprising a protein transduction domain.

The present invention also contemplates a polypeptide as described above attached to glutathione-S-transferase (GST), optionally via a spacer molecule. The spacer molecule may be any spacer molecule known in the art. Polypeptide spacer molecules, non-polypeptide spacer molecules and combinations thereof are contemplated herein.

Also provided is a polypeptide as described above covalently attached to a protein carrier, a non-protein carrier or a solid support.

The present invention also provides a nucleic acid encoding a polypeptide as described above.

Also provided by the present invention is a method of identifying an agent that inhibits the interaction of D2R with DISC1, the method comprising, a) testing an agent in a cell culture system, said cell culture system comprising cells wherein the D2R associates with DISC1, the testing comprising treating the cells with the agent or alternatively, expressing a nucleic acid in the cells to produce a polypeptide agent, and;

b) determining if the agent or polypeptide agent inhibits the interaction of D2R with DISC1.

Also provided by the present invention is a method of identifying an agent that binds to the polypeptide as described above, the method comprising contacting a polypeptide sequence comprising SEQ ID NO:1 with one or more agents and determining if the one or more agents bind to SEQ ID NO:1.

Also contemplated by the present invention is a method of inhibiting D2R interaction with DISC1 in a mammal comprising administering an agent that inhibits the interaction of D2R with DISC1 in the mammal.

In a further embodiment, which is not meant to be limiting, there is provided a polypeptide comprising the amino acid sequence MPGGGPQGAPAAAGGGGVSHRAGSRD-CLPPAACFRRRRLARRPGYMRSSTG PGIGEL-SPAVGTLFREPGGVSGEE (SEQ ID NO:5), a fragment thereof; or a polypeptide comprising an amino acid sequence that is at least 80% identical to SEQ ID NO:5, or a fragment thereof, wherein the polypeptide is not a naturally occurring DISC1 protein. In a specific, non-limiting embodiment the N terminal methionine is removed.

Also provided is a polypeptide as described above comprising a protein transduction domain. In a further embodiment the polypeptide is covalently or non-covalently attached to a protein carrier, a non-protein carrier or a solid support.

Also provided is a nucleic acid encoding the polypeptide as described above.

There is also provided a method of identifying an agent that binds to the polypeptide sequence defined by SEQ ID NO:5, the method comprising contacting a polypeptide sequence comprising SEQ ID NO:5 with one or more agents and determining if the one or more agents bind to SEQ ID NO:5.

Also contemplated is a kit comprising any polypeptide, nucleic acid, protein carrier, non-protein carrier, solid support, reagent, solution or any combination thereof as described herein and optionally instructions for using any element or combination of elements therein.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 8A shows results of an in vitro binding assay, demonstrating that [35S]-DISC1NT probe, but not [35S]-DISC1CT probe, bound with GST-D2IL3-1-1. These data suggest that D2R interacts with the N-terminal of DISC1 directly. FIG. 8B shows results of mapping the interaction site of D2R-DISC1 on DISC1 by using an affinity pull-down technique. D2R is pulled down by the GST-DISC1-NT-1, but not by other GST-DISC1-NT segments or GST alone in rat striatal tissue. FIG. 8C shows a schematic representation of GST-fusion proteins encoding truncated DISC1-NT segments 1-5.

DETAILED DESCRIPTION

Figure 1:
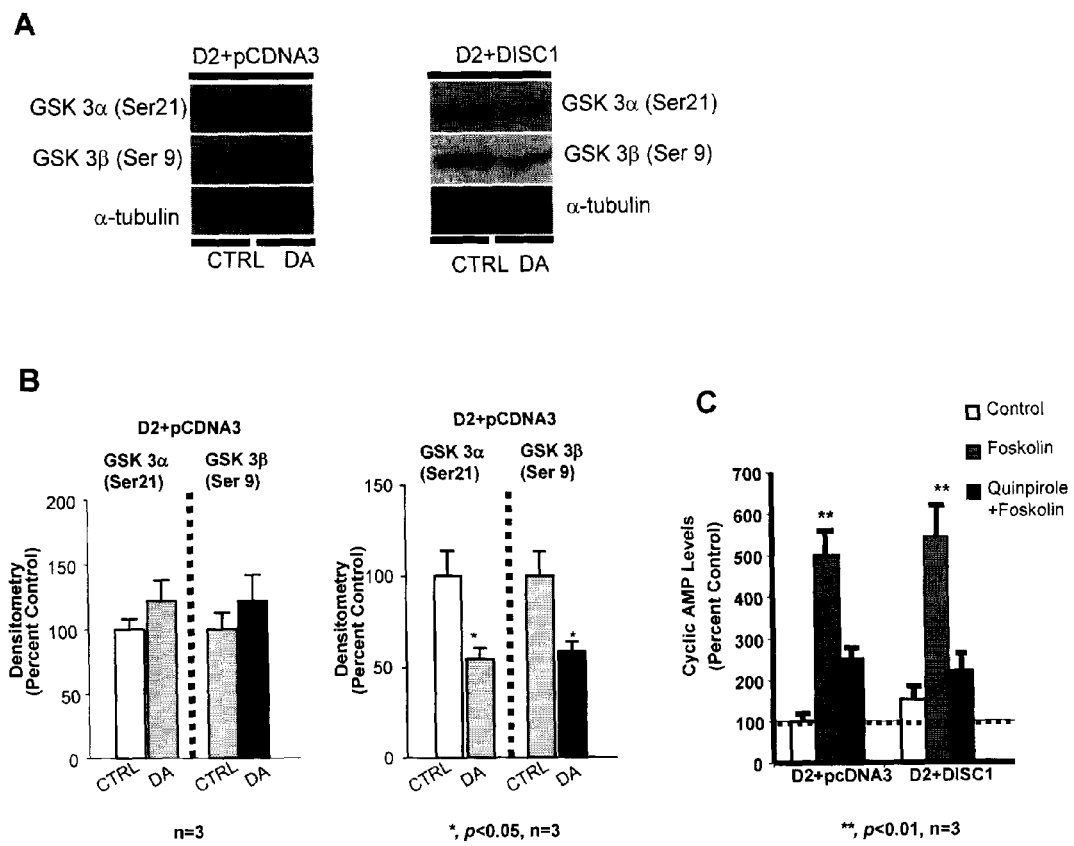
FIGS. 1A-1C show evidence of DISC1 in D2R cAMP-independent signaling pathway. (A) Western blot analysis of phosphorylated GSK-3α/β levels in extract prepared from transfected HEK293T cells in the presence or absence of DA. Alpha-tubulin was used as loading controls. (B) Densitometric analysis. Data are analyzed by t-test. (C) Cyclic AMP analysis in transfected HEK293T cells in the presence or absence of Foskolin and Quinpirole. Data are analyzed by one-way ANOVA. Data are means±SEM. Numbers of samples per group (n) are indicated. CTRL: Control; DA: Dopamine.

The present invention relates to compositions and methods for modulating D2R-DISC1 interaction.

The following description is of a preferred embodiment.

Disrupted-in-schizophrenia-1 (DISC1) has recently emerged as one of the most promising candidate genes affecting susceptibility to schizophrenia. However, little is known regarding the potential mechanisms through which DISC1 may influence risk for schizophrenia. We report here novel findings regarding the regulation of D2R signaling by DISC1. Specifically, we have found that co-expression of DISC1 with D2R in HEK-293T cells leads to the reduction of glycogen synthase kinase (GSK)-3 phosphorylation upon agonist stimulation of D2R, consistent with observations in rat striatum. In contrast, D2R activation failed to alter GSK-3 phosphorylation in HEK-293T cells expressing D2R with pcDNA3, the mammalian vector in which DISC1 is subcloned. Second, using co-immunoprecipitation methods, we have found that D2R forms a protein complex with DISC1 in rat striatum. Third, using affinity purification methods, we have identified the 15 amino-acid polypeptide within the third intracellular loop of D2R that enables the D2: DISC1 complex formation. Fourth, disruption of the D2-DISC1 interaction, by co-expressing the mini-gene encoding the interacting site in HEK-293T cells expressing D2R and DISC1, abolished the D2-induced reduction of GSK-3 phosphorylation. Fifth, D2R-DISC1 coupling is significantly enhanced in a DISC1 mutant mouse model displaying schizophrenia-like behaviours. We have also determined the corresponding interacting site on DISC1 as described below.

The present invention provides a polypeptide comprising the amino acid sequence KIYIVLRRRRKRVNT (SEQ ID NO:1), a fragment thereof, or a polypeptide comprising an amino acid sequence that is at least 80% identical to SEQ ID NO:1, or a fragment thereof.

In an embodiment, which is not meant to be limiting in any manner, the polypeptide comprises a fragment of SEQ ID NO:1, the fragment comprising at least about 5 continuous amino acids of SEQ ID NO:1, for example 5, 6, 7, 8, 9, 10, 11, 12, 13, 14 or 15 continuous amino acids.

It is to be understood that the polypeptide described above may form part of a larger polypeptide or protein but does not comprise or consist of a naturally occurring dopamine receptor. For example, but not to be limiting in any manner, the polypeptide may comprise about 5 or more amino acids in length, for example, but not limited to 5, 6, 7, 8, 9, 10, 11, 12, 13, 14, 15, 20, 25, 30, 35, 40, 50, 60, 70, 80, 90, 100, 120, 150, 180, 200 or more amino acids. It is also to be understood that the size of the polypeptide may be defined by a range of any two of the values listed above and any two values therein between.

The present invention also contemplates polypeptides having an amino acid sequence that comprises 80%, 81%, 82%, 83%, 84%, 85%, 86%, 87%, 88%, 89%, 90%, 91%, 92%, 93%, 94%, 95%, 96%, 97%, 98%, 99% or 100% identity to the amino sequences described above. Further, the polypeptides may be defined as comprising a range of sequence identity defined by any two of the values listed above, or any two values therein between.

The present invention also provides a nucleic acid encoding polypeptides as defined above. For example, but not wishing to be limiting in any manner, the present invention contemplates a nucleic acid encoding a polypeptide comprising the amino acid sequence KIYIVLRRRRKRVNT (SEQ ID NO:1), a fragment thereof, or a polypeptide comprising an amino acid sequence that is at least 80% identical to SEQ ID NO:1, or a fragment thereof. The nucleic acid does not comprise a nucleotide sequence encoding a naturally occurring dopamine receptor.

To determine whether a nucleic acid exhibits identity with the sequences presented herein, oligonucleotide or protein alignment algorithms may be used, for example, but not limited to a BLAST (Altschul, S., et al., *J. Mol. Bio.*, Vol. 215(3), pp. 403-410 (1990)), BLAST2 (Lipman and Pearson, *Science*, Vol. 227(4693), pp. 1435-1441 (1985)), or FASTA, search, using default parameters. Polypeptide alignment algorithms are also available, for example, without limitation, BLAST 2 Sequences (Temple S. Smith and Michael S. Waterman. *J. Mol. Bio.*, Vol. 147, pp. 195-197 (1981)).

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. for at least 1 hour (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. for at least 1 hour (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part 1, Chapter 2 "Overview of principles of hybridization and the strategy of nucleic acid probe assays", Elsevier, N.Y.). Generally, but not wishing to be limiting, stringent conditions are selected to be about 5° C. lower than the thermal melting point for the specific sequence at a defined ionic strength and pH.

The polypeptide or nucleic acid encoding the polypeptide of the instant application may be bound to protein transduction domain. By "protein transduction domain" it is meant an amino acid sequence that facilitates transport of the polypeptide, or facilitates localization to a particular site, for example a cell or the like, or it may facilitate transport across a membrane or lipid bilayer. The polypeptides and nucleic acids of the present invention may be fused to a protein transduction domain to facilitate transit across lipid bilayers or membranes and the like.

Many polypeptides and nucleic acids do not efficiently cross the lipid bilayer of the plasma membrane, and therefore enter into cells at a low rate. However, there are certain naturally occurring polypeptides that can transit across membranes independent of any specific transporter. Antennapedia (Drosophila), TAT (HIV) and VP22 (Herpes) are examples of such polypeptides, herein also termed protein transduction domains. Fragments of these and other polypeptides have been shown to retain the capacity to transit across lipid membranes in a receptor-independent fashion. These molecules are generally 10 to 27 amino acids in length, possess multiple positive charges, and in several cases have been predicted to be amphipathic. Polypeptides and nucleic acids that are normally inefficient or incapable of crossing a lipid bilayer, can be made to transit the bilayer by being fused to a protein transduction domain.

U.S. Publication 2002/0142299 (which is incorporated herein by reference) describes a fusion of TAT with human beta-glucuronidase. This fusion protein readily transits into various cell types both in vitro and in vivo. Furthermore, TAT fusion proteins have been observed to cross the blood-brain-barrier. Frankel et al. (U.S. Pat. No. 5,804,604, U.S. Pat. No. 5,747,641, U.S. Pat. No. 5,674,980, U.S. Pat. No. 5,670,617, and U.S. Pat. No. 5,652,122; which are incorporated herein by reference) have also demonstrated transport of a protein (beta-galactosidase or horseradish peroxidase) into a cell by fusing the protein with amino acids 49-57 of TAT.

PCT publication WO01/15511 (which is incorporated herein by reference) discloses a method for developing protein transduction domains using a phage display library. The method comprises incubating a target cell with a peptide display library and isolating internalized peptides from the cytoplasm and nuclei of the cells and identifying the peptides. The method further comprises linking the identified peptides to a protein and incubating the peptide-protein complex with a target cell to determine whether uptake is facilitated. Using this method a protein transduction domain for any cell or tissue type may be developed. US Publication 2004/0209797 (which is incorporated herein by reference) shows that reverse isomers of several of the peptides identified by the above can also function as protein transduction domains.

PCT Publication WO99/07728 (which is incorporated herein by reference) describes linearization of protegrin and tachyplesin, naturally occurring as a hairpin type structure held by disulphide bridges. Irreversible reduction of disulphide bridges generated peptides that could readily transit cell membranes, alone or fused to other biological molecules. US Publication 2003/0186890 (which is incorporated herein by reference) describes derivatives of protegrin and tachyplesin that were termed SynB1, SynB2, SynB3, etc. These SynB peptides were further optimized for mean hydrophobicity per residue, helical hydrophobic moment (amphipathicity), or beta hydrophobic moment. Various optimized amphipathic SynB analog peptides were shown to facilitate transfer of doxorubicin across cell membranes. Further, doxorubicin linked to a SynB analog was observed to penetrate the blood-brain-barrier at 20 times the rate of doxorubicin alone.

The protein transduction domains described in the proceeding paragraphs are only a few examples of the protein transduction domains available for facilitating membrane transit of small molecules, polypeptides or nucleic acids. Other examples are transportan, W/R, AlkCWK18, DipaLytic, MGP, or RWR. Still many other examples will be recognized by persons skilled in the art The polypeptides as described herein can be synthesized in vitro or delivered to a cell in vivo by any conventional method. As a representative example of an in vitro method, the polypeptide may be chemically synthesized in vitro, or may be enzymatically synthesized in vitro in a suitable biological expression system. As a representative example of an in vivo method, a DNA, RNA, or DNA/RNA hybrid molecule comprising a nucleotide sequence encoding a polypeptide of the invention is introduced into an animal, and the nucleotide sequence is expressed within a cell of an animal. Alternatively, the polypeptide of the present invention may be administered directly to a subject in need thereof, for example, but not limited to by injection or the like.

Nucleotide sequences encoding polypeptides may be operably linked to regulatory elements in order to achieve preferential expression at desired times or in desired cell or tissue types. Furthermore, as will be known to one of skill in the art, other nucleotide sequences including, without limitation, 5' untranslated region, 3' untranslated regions, cap structure, poly A tail, translational initiators, sequences encoding signalling or targeting peptides, translational enhancers, transcriptional enhancers, translational terminators, transcriptional terminators, transcriptional promoters, may be operably linked with the nucleotide sequence encoding a polypeptide (see as a representative examples "Genes VII", Lewin, B. Oxford University Press (2000) or "Molecular Cloning: A Laboratory Manual", Sambrook et al., Cold Spring Harbor Laboratory, 3rd edition (2001)). A nucleotide sequence encoding a polypeptide or a fusion polypeptide comprising a polypeptide as described above and a protein transduction domain may be incorporated into a suitable vector. Vectors may be commercially obtained from companies such as Stratagene or InVitrogen. Vectors can also be individually constructed or modified using standard molecular biology techniques, as outlined, for example, but not limited to as described in Sambrook et al. (Cold Spring Harbor Laboratory, 3rd edition (2001)). A vector may contain any number of nucleotide sequences encoding desired elements that may be operably linked to a nucleotide sequence encoding a polypeptide or fusion polypeptide comprising a protein transduction domain. Such nucleotide sequences encoding desired elements, include, but are not limited to, transcriptional promoters, transcriptional enhancers, transcriptional terminators, translational initiators, translational, terminators, ribosome binding sites, 5' untranslated region, 3' untranslated regions, cap structure, poly A tail, origin of replication, detectable markers, affinity tags, signal or target peptide. Persons skilled in the art will recognize that the selection and/or construction of a suitable vector may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

A DNA, RNA, or DNA/RNA hybrid molecule may be introduced intracellularly, extracellularly into a cavity, interstitial space, into the circulation of an organism, orally, or by any other standard route of introduction for therapeutic molecules and/or pharmaceutical compositions. Standard physical methods of introducing nucleic acids include, but are not limited to, injection of a solution comprising RNA, DNA, or RNA/DNA hybrids, bombardment by particles covered by the nucleic acid, bathing a cell or organism in a solution of the nucleic acid, or electroporation of cell membranes in the presence of the nucleic acid.

Dosage Forms

The polypeptide or nucleic acids encoding polypeptides as described herein may be formulated into any convenient dosage form. The dosage form may comprise, but is not limited to an oral dosage form wherein the polypeptide, nucleic acid or both is dissolved, suspended or the like in a suitable excipient, such as, but not limited to water, a buffer or another carrier. In addition, the polypeptide or nucleic acids as described herein may be formulated into a dosage form that could be administered by injection, for example, but not limited to, subcutaneous, intravenous, intracranial injection, or the like. An injectable dosage form may include one or carriers or other pharmaceutically acceptable excipients that may function to enhance the delivery and/or activity of the polypeptide or nucleic acid. Any suitable carrier known in the art may be used. Also, the polypeptide or nucleic acids encoding same may be formulated for use in the production of a medicament. Many methods for the production of dosage forms, medicaments, or pharmaceutical compositions are well known in the art and can be readily applied to the present invention by persons skilled in the art.

Methods

The present invention also contemplates a method of identifying an agent that inhibits the interaction of D2R with DISC1, the method comprising testing an agent in a cell culture system, said cell culture system comprising cells wherein the D2R associates with DISC1, treating the cells with the agent or alternatively, expressing a nucleic acid in the cells to produce a polypeptide agent, and determining if the agent or polypeptide agent inhibits the interaction of D2R with DISC1.

By "agent" it is meant any small molecule chemical compound, polypeptide, nucleic acid, protein, antibody, antibody fragment or the like that can inhibit the interaction of D2R with DISC1.

The present invention also provides a method of identifying an agent that binds to the polypeptide sequence defined by SEQ ID NO:1, the method comprising contacting a polypeptide sequence comprising SEQ ID NO:1 with one or more agents and determining if the one or more agents bind to SEQ ID NO:1.

The present invention also contemplates a method of inhibiting D2R interaction with DISC1 in a mammal comprising administering an agent that inhibits the interaction of D2R with DISC1 to the mammal. Any mammal including, without limitation, human, rat, cow, pig, dog, or mouse, may be treated with the agent according to the method of the present invention.

The present invention also provides a polypeptide comprising the amino acid sequence MPGGGPQGAPAAAGGGGVSHRAGSRDCLPPAACFRRRRLARRPGYMRSSTG PGIGFLSPAVGTLFRFPGGVSGEE (SEQ ID NO:5), a fragment thereof, or a polypeptide comprising an amino acid sequence that is at least 80% identical to SEQ ID NO:5, or a fragment thereof.

In an embodiment, which is not meant to be limiting in any manner, the polypeptide comprises a fragment of SEQ ID NO:5, the fragment comprising at least about 5 continuous amino acids of SEQ ID NO:5, for example 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 continuous amino acids.

It is to be understood that the polypeptide described above may form part of a larger polypeptide or protein but does not comprise or consist of a naturally occurring DISC1 protein, for example, but not limited to: MPGGGPQGAPAAAGGGGVSHRAGSRDCLPPAACFRRRRLARRPGYMRSSTG PGIGFLSPAVGTLFRFPGGVSGEESHHSESRARQCGLDSRGLLVRSPVSKSAAA PTVTSVRGTSAHEGIQLRGGTRLPDRLSWPCGPGSAGWQQEFAAMDSSETLD ASWEAACSDGARRVRAAGSLPSAELSSNSCSPGCGPEVPPTPPGSHSAFTSSFS FIRLSLGSAGERGEAEGCPPSREAESHCQSPQEMGAKAASLDGPHEDPRCLSR PFSLLATRVSADLAQAARNSSRPERDMHSLPDMDPGSSSSLDPSLAGCGGDGS SGSGDAHSWDTLLRKWEPVLRDCLLRNRRQMEVISLRLKLQKLQEDAVEND DYDKAETLQQRLEDLEQEKISLHFQLPSRQPALSSFLGHLAAQVQAALRRGAT QQASGDDTHTPLRMEPRELEPTAQDSLHVSITRRDWELQEKQQLQKEIEALQA RMFVLEAKDQQLRREIEEQEQQLQWQGCDLTPLVGQLSLGQLQEVSKALQDT LASAGQIPFHAEPPETIRSLQERIKSLNLSLKEITTKVCMSEKFCSTLRKKVNDIE TQLPALLEAKIVIHAISGNHFWTAKDLTEEIRSLTSEREGLEGLLSKLLVLSSRNV KKLGSVKEDYNRLRREVEHQETAYETSVKENTMKYMETLKNKLCSCKCPLL GKVWEADLEACRLLIQSLQLQEARGSLSVEDERQMDDLEGAAPPIPPRLHSED KRKTPLKVLEEWKTHLIPSLHCAGGEQKEESYILSAELGEKCEDIGKKLLYLED QLHTAIHSHDEDLIQSLRRELQMVKETLQAMILQLQPAKEAGEREAAASCMT AGVHEAQA (SEQ ID NO:6). In an embodiment, but not to be limiting in any manner, the polypeptide may comprise about 5 or more amino acids in length, for example, but not limited to 5, 6, 7, 8, 9, 10, 11, 12, 13, 14, 15, 20, 25, 30, 35, 40, 50, 60, 70, 80, 90, 100, 120, 150, 180, 200 or more amino acids. It is also to be understood that the size of the polypeptide may be defined by a range of any two of the values listed above and any two values therein between.

The present invention also contemplates polypeptides having an amino acid sequence that comprises 80%, 81%, 82%, 83%, 84%, 85%, 86%, 87%, 88%, 89%, 90%, 91%, 92%, 93%, 94%, 95%, 96%, 97%, 98%, 99% or 100% identity to the amino sequences described above. Further, the polypeptides may be defined as comprising a range of sequence identity defined by any two of the values listed above, or any two values therein between.

The present invention also provides a nucleic acid encoding polypeptides as defined above. For example, but not wishing to be limiting in any manner, the present invention contemplates a nucleic acid encoding a polypeptide comprising the amino acid sequence MPGGGPQGAPAAAGGGGVSHRAGSRDCLPPAACFRRRRLARRPGYMRSSTG PGIGFLSPAVGTLFRFPGGVSGEE (SEQ ID NO:5), a fragment thereof, or a polypeptide comprising an amino acid sequence that is at least 80% identical to SEQ ID NO:5, or a fragment thereof. The nucleic acid does not comprise a nucleotide sequence encoding a naturally occurring DISC1 protein, for example as shown in SEQ ID NO:6.

The polypeptide or nucleic acid encoding the polypeptide of the instant application may be bound to protein transduction domain, solid support, bead, protein carrier, non-protein carrier or the like as described herein.

The present invention also provides a method of identifying an agent that binds to the polypeptide sequence defined by SEQ ED NO:5, the method comprising contacting a polypeptide sequence comprising SEQ ID NO:5 with one or more agents and determining if the one or more agents bind to SEQ ID NO:5.

The present invention will be further illustrated in the following examples.

EXAMPLES

Example I

Activation of D2R Decreased GSK-3 Phosphorylation in HEK-293T Cells Co-Expressing DISC1 and D2R Currently, all studies related to D2R-mediated Akt/GSK-3 signaling were carried out in brain tissue, where the expression of D2R and DISC1 was confirmed (11,89,99). At least to our knowledge, there are no studies of D2R-mediated Akt/GSK-3 signaling in HEK-293T cells. Furthermore, there is no evidence indicating the existence of endogenous DISC1 in HEK-293T cells. Thus, an initial step to investigate whether DISC1 is involved in D2R-mediated Akt/GSK-3 signaling is to compare the activation of D2R-induced reduction of GSK-3 phosphorylation in HEK-293T cells co-expressing DISC1 and D2R with that in HEK-293T cells expressing D2R with pcDNA3—the mammalian expression vector in which DISC1 is subcloned. We have initially chosen to use D2L instead of D2S based on previous studies that have shown that the D2S is the predominant presynaptic D2R while D2L is preferentially involved in postsynaptic signaling (20-25). As shown in FIG. 1A, pre-incubating the HEK-293T cells co-expressing D2R and DISC1 with 10 μM dopamine (30 min) significantly decreased phosphorylation of GSK3α/β, as illustrated in Western blot with primary antibody against phosphor-GSK-3α/β Ser-21/9. In contrast, dopamine stimulation failed to alter the phosphorylation of GSK3α/β in cells expressing D2R with pcDNA3 (mammalian vector in which DISC1 is subcloned) indicating that DISC1 is required for D2R-induced reduction of GSK3α/β phosphorylation. This experiment was repeated three times. The intensity of phosphor-GSK-3α Ser-21 and GSK-3α Ser-9 binding was quantified by densitometry (software: AIS Imaging Research Inc) (FIG. 1B). α-actin acted as a loading control in this experiment.

We also tested whether DISC1 is involved in D2R-mediated cAMP accumulation. Thus, we measured D2R-mediated cAMP accumulation in both HEK-293T cells co-expressing DISC1, and D2R and HEK-293T cells expressing D2R with pcDNA3. The cells were treated with fosculin (1 µM, 10 min at 37° C.) with/without pretreatment with 10 µM dopamine (30 min). We concluded that there is no difference in D2R-medaited cAMP accumulation between these two groups (n=3) (FIG. 1C). These data indicated that DISC1 is involved in D2R-mediated Akt/GSK-3 signaling.

Example II

DISC1 Forms a Protein Complex with D2R

Figure 2:
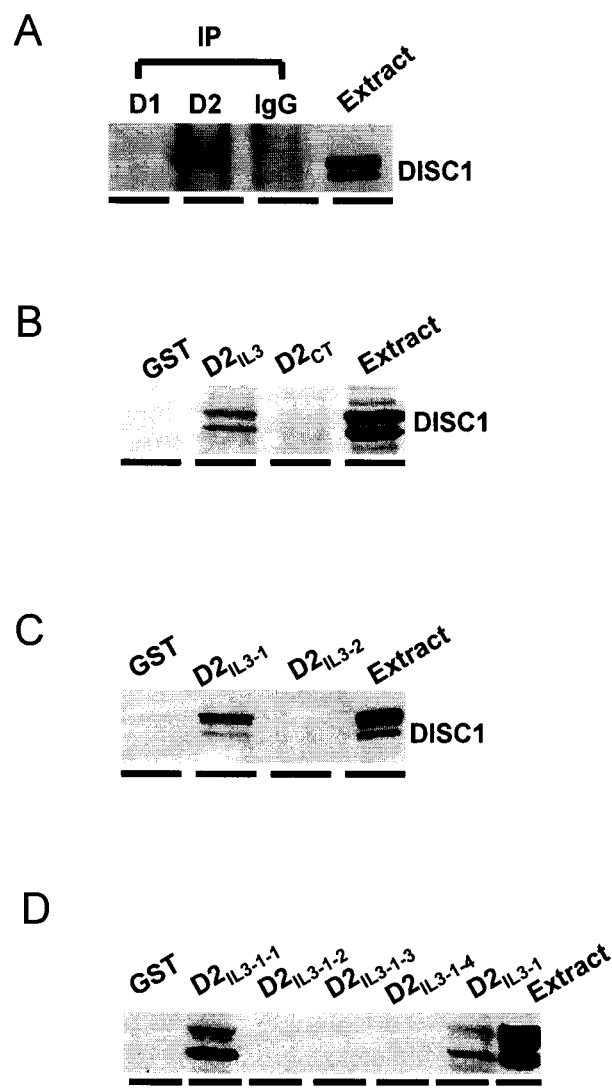
FIGS. 2A-2D show results of association of Dopamine D2 receptor and DISC1. (A) Co-immunoprecipitation of DISC1 by D2 antibody in rat striatal tissue. (B) Affinity pull-down of the DISC1 by the GST-D2IL3 but not by GST-D2CT, or GST alone in rat striatal tissue. (C) Affinity pull-down of the DISC1 by the GST-D2IL3-1 but not by GST-D2IL3-2IL3-1-1; (D) Affinity pull-down of the DISC1 by the GST-D2IL3-1-1 but not by other GST fusion proteins or GST alone in rat striatal tissue.

As discussed previously, D2R function can be regulated by D2R-interacting proteins. Thus, in an attempt to define the structural basis for the observed reduction of GSK3α/β phosphorylation when DISC1, is co-expressed with D2R, we hypothesized that D2R and DISC1 may form a protein complex and this D2-DISC1 protein-protein interaction may be responsible for the observed effect of DISC1 co-expression on GSK3α/β phosphorylation. As shown in FIG. 2A, we have identified the existence of a D2R: DISC1 complex in rat striatal tissue using co-immunoprecipitation method with primary antibody against D2R. In contrast, D1R antibody failed to co-immunoprecipitate with DISC1, while the direct immunoprecipitation of D1R verified both D1R expression and the efficiency of the antibody for Immunoprecipitation (data not shown).

Example III

Identification of the Specific Region(s) of the D2R that Enable D2R and DISC1 to Form a Complex Using Affinity Purification This method uses GST fusion proteins encoding the fragments of a test protein to affinity purify other proteins that may form complexes with the test protein in tissue from a specific brain region. Since DISC1 is an intracellular protein, we made GST-fusion proteins encoding two intracellular regions of D2R: the carboxyl tail (CT) of D2R (D2CT: T428-C443) and the third intracellular loop (ID) of D2R (D2IL3: K211-Q373). Many dopamine receptor interacting proteins have been identified that interact with either the CT or the IL3 region of dopamine receptors (94). Using the affinity purification method, we determined that the site responsible for D2R-DISC1 complex formation is limited to the third intracellular region of D2R, since only GST-D2IL3, but not GST-D2CT or GST alone, recognizes and precipitates DISC1 from solubilized striatal tissues (FIG. 2B). To confirm this result and to further delineate the specific region of the D2IL3 involved in the D2R-DISC1 interaction, we further dissected the D2IL3 into two fragments D2IL3-1: K211-V270 and D2IL3-2: E271-Q373. GST fusion proteins encoding these two fragments were made and used in the affinity purification experiment. As shown in FIG. 2C, GST-D2IL3-1 recognizes and precipitates DISC1 from solubilized striatal tissues, while GST-D2IL3-2 or GST alone failed to "pull down" DISC1. We further dissected the D2IL3-1 into four fragments: D2IL3-1-1: K211-T225; D2IL3-1-2: K226-L240; D2IL3-1-3: K241-V255; D2IL3-1-4: I256-V270 and affinity purification experiment indicated that GST-D2IL3-1-1 (SEQ ID NO:1) recognizes and precipitates DISC1 from solubilized striatal tissues, while GST-D2IL3-1-2, GST-D2IL3-1-3 GST-D2IL3-1-4 or GST alone failed to "pull down" DISC1 (FIG. 2D). Thus, we concluded that D2IL3-1-1 (SEQ ID NO:1) comprises the site for D2-DISC1 interaction.

Figure 3:
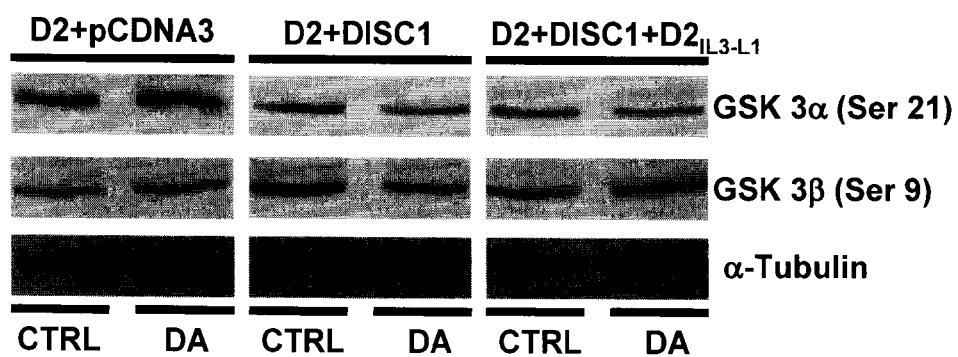
FIG. 3 shows results of western blot analysis of phosphorylated GSK-3α/β (Ser21/9) levels in extract prepared from transfected HEK293T cells co-expressing D2+pCDNA3 (left), D2+DISC1 (middle) or D2+DISC1+D2IL3-L1 (right) in the presence or absence of DA. Alpha-tubulin was used as loading controls. CTRL: Control; DA: Dopamine.

As discussed above, previous studies have demonstrated that activation of D2R decreases phosphorylation of Thr-308-Akt and GSK-3α/β in rat striatum (27-28, 101-103). Without wishing to be limiting or bound by theory, if the D2R-mediated reduction of phosphorylation of Thr-308-Akt and GSK-3α/β were a sole product of the D2-DISC1 protein-protein interaction, mini-genes encoding these binding sites of D2R or DISC1 will block the D2-DISC1 interaction and abolish the observed D2R-induced reduction of Thr-308-Akt and GSK-3α/β phosphorylation. We have obtained data showing that the ability of the D2R activation to reduce GSK-3α/β phosphorylation (antibodies: anti-phospho-GSK-3α/β Ser-21/9) was abolished by co-expression of the D2IL3-1 mini-gene, but not by co-expression of the vector pcDNA3 (FIG. 3). We did not use the D2IL3-2 mini-gene as the control since several proteins (e.g. dopamine transporter) are reported to couple with D2R via this region. The D2IL3-1 mini-gene results are consistent with D2-DISC1 interaction being responsible for the D2R-mediated reduction of GSK-3α/β phosphorylation.

Figure 4:
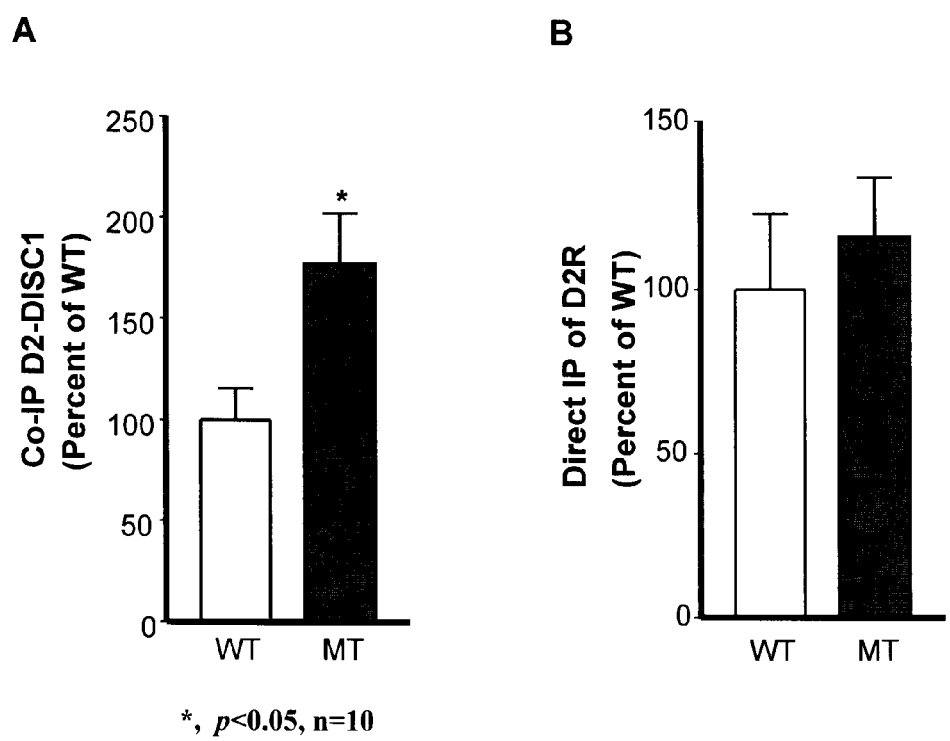
FIGS. 4A-4B show results characterizing D2-DISC1 receptor complex formation in DISC1 mutant mice. (A) Mice striatal brain samples were incubated with D2R antibodies for coimmunoprecipitation experiments. Precipitated proteins were subject to SDS-PAGE and then immunoblotted with DISC1 antibody. (B) Direct immunoprecipitation of D2R with D2R antibodies. Data are means±SEM. and are analyzed by t-test. Numbers of samples per group (n) are indicated. WT: Wild type; MT: DISC1 Mutant.
Figure 5:
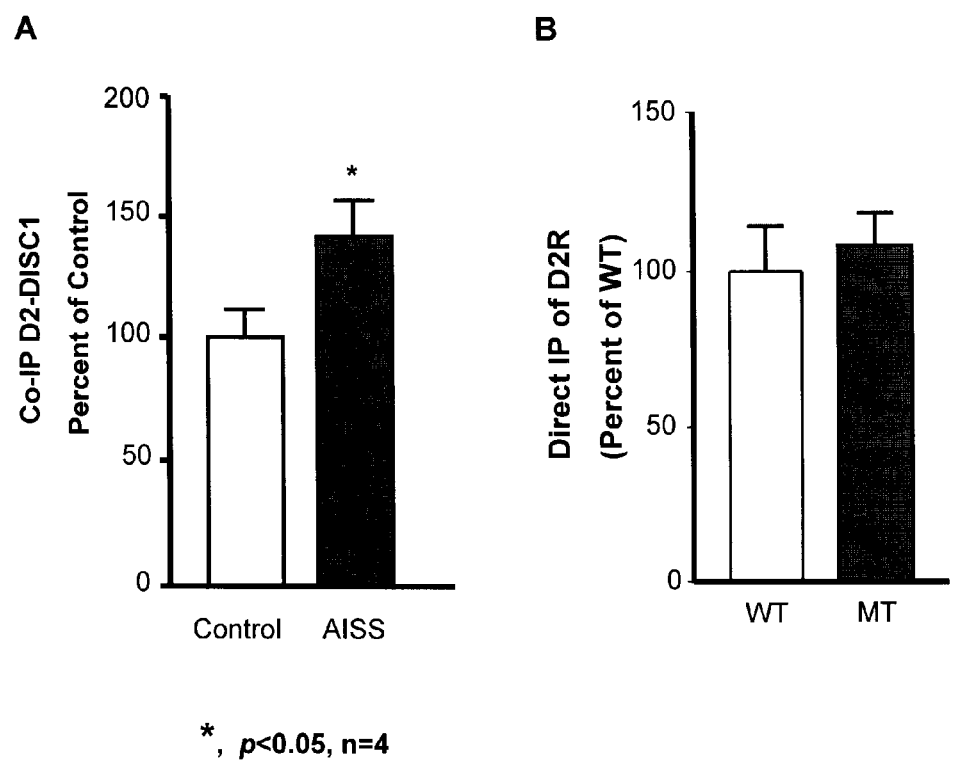
FIGS. 5A-5B show results characterizing D2-DISC1 receptor complex formation in rat AISS model. (A) Rat striatal brain samples were incubated with D2R antibodies for coimmunoprecipitation experiments. Precipitated proteins were subject to SDS-PAGE and then immunoblotted with DISC1 antibody. (B). Direct immunoprecipitation of D2R with D2R antibodies. Data are means±SEM. and are analyzed by t-test. Numbers of samples per group (n) are indicated. AISS: Amphetamine-Induced Sensitized State.

The D2-DISC1 protein-protein interaction is significantly enhanced in striatal tissue of animal models of schizophrenia. Previous studies have shown that DISC1 mutant mice (L100P DISC1 mutant) display schizophrenia-like behaviours (90). Using a co-immunoprecipitation method, we have shown that the D2-DISC1 interaction is significantly enhanced in these DISC1 mutant mice compared to wild-type mice, while the directly immunoprecipitated D2R was not changed (FIG. 4). We also tested the D2-DISC1 interaction in another widely used animal model of schizophrenia, the AISS rat (amphetamine-induced-sensitized-state). Consistent with the result from the L100P DISC1 mutant mice, the D2-DISC1 interaction is significantly enhanced in striatal tissue of AISS rats (FIG. 5).

Example IV

Figure 6:
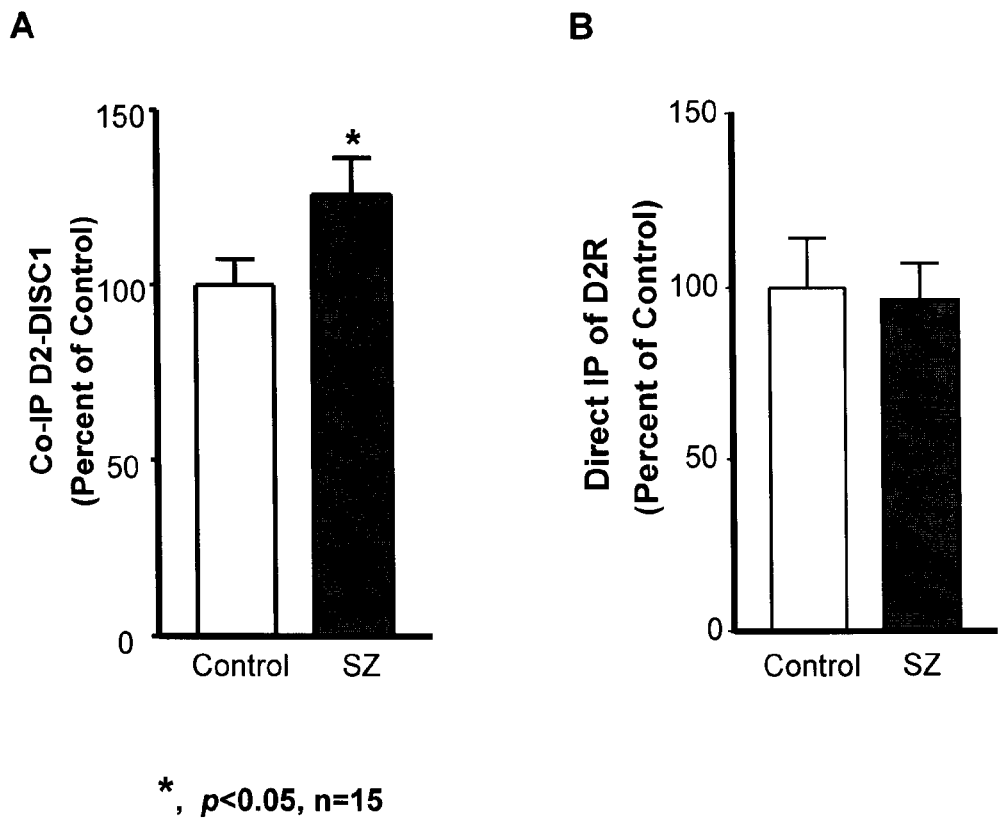
FIGS. 6A-6B show results characterizing the D2-DISC1 receptor complex formation in human brains from Stanley Foundation. (A) Human striatal brain samples were incubated with D2R antibodies for coimmunoprecipitation experiments. Precipitated proteins were subject to SDS-PAGE and then immunoblotted with DISC1 antibody. (B) Direct immunoprecipitation of D2R with D2R antibodies. Data are means±SEM. and are analyzed by t-test. Numbers of samples per group (n) are indicated. SZ: Schizophrenia.

The D2-DISC1 Protein-Protein Interaction is Significantly Enhanced in the Post-Mortem Brains of Schizophrenia Patients and Animal Models of Schizophrenia Both DISC1 and D2R have been implicated in the pathology of mental illness. Thus, we determined if the observed interaction between D2R and DISC1 is altered in post mortem brains of schizophrenia patients. This was tested by co-immunoprecipitation of the DISC1 by the D2R antibody from solubilized striatal tissue from 30 post-mortem brain samples (15 control, 15 schizophrenia,) from the Stanley Foundation. These subjects were matched for age, sex, time from death to tissue freezing, and drug history where possible. Detailed drug histories for these samples have been published previously (107-108). The co-immunoprecipitated proteins recognized by the D2 antibody was immunoblotted with DISC1 antibodies and the intensity of each protein band was quantified by densitometry. Each co-immunoprecipitation was in parallel with western blot analysis of the initial levels of solubilized protein and directly immunoprecipitated proteins. As shown in FIG. 6, the D2-DISC1 interaction is significantly enhanced in the post-mortem brain tissue of schizophrenia patients compare to control subjects, while the directly immunoprecipitated D2R was not changed.

Example V

Figure 7:
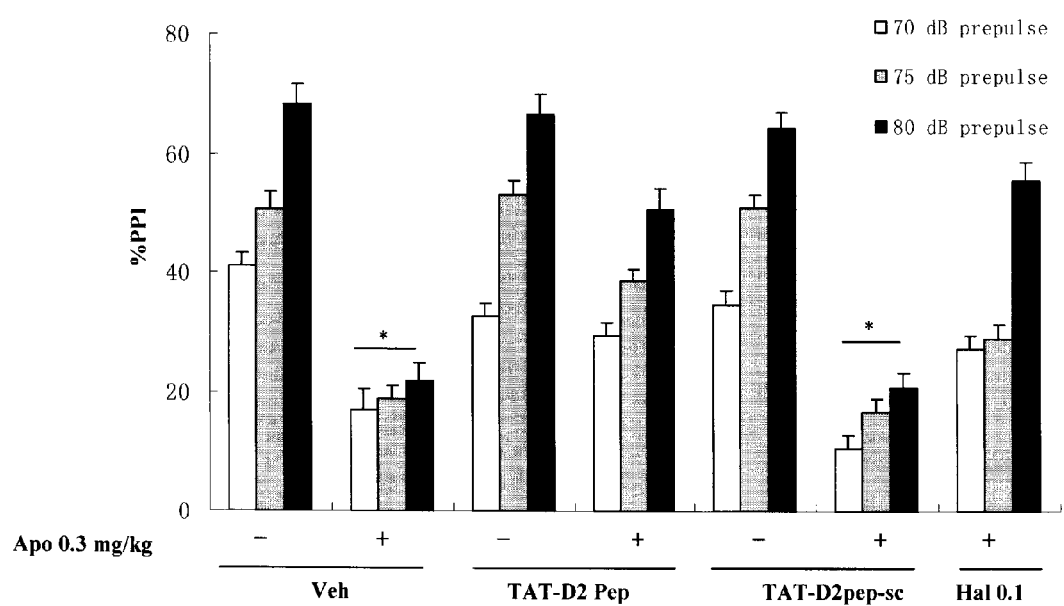
FIG. 7 shows results that TAT-D2pep (1 mM, 4 μl, ICV) blocked the effect of apomorphine to disrupt PPI. In control rats (Veh−) increasing the prepulse stimulus intensity increased the amount of PPI. Rats treated with apomorphine (Veh+) showed reduced levels of PPI at all 3 prepulse intensities ($p<0.05$). TAT-D2pep completely reversed the effects of apomorphine (0.3 mg/kg), without altering the degree of PPI. The scrambled peptide (TAT-D2pep-sc) did not affect the response to apomorphine, or the basal PPI effect. The D2 receptor antagonist haloperidol also reversed the effect of apomorphine, especially at the higher two prepulse intensities. (n=5 per group).

Disruption of D2-DISC1 Interaction Significantly Reversed the Disruption of Pre-Pulse Inhibition (PPI) Induced by Apomorphine in Rats PPI of the acoustic startle reflex is a sensorimotor gating process known to be deficient in a number of neurologic and psychiatric conditions including, but not limited to schizophrenia, Huntington's disease, Tourette's syndrome, and obsessive compulsive disorder (OCD). PPI can be disrupted by the dopamine D1/D2R agonist apomorphine in rats (111). Antipsychotics that have affinity for D2R such as haloperidol prevent the apomorphine-induced deficits (111-113). Furthermore, disruption of PPI was observed in DISC1-L100P mutant mice and inhibition of GSK-3 activity in vivo significantly normalized PPI in DISC1-L100P. Accordingly, if D2-DISC1 interaction plays an important role in the D2R-mediated reduction of phosphorylation of GSK-3α/β, disruption of the D2R-DISC1 interaction should reverse D2R-associated behaviours such as PPI deficit. As shown in FIG. 7, apomorphine (0.3 mg/kg, SC) significantly disrupted PPI in comparison with saline (P<0.05, n=5/group), and this effect was blocked by haloperidol (0.1 mg/kg, SC). Intraventricular (ICV) injection of TAT-D2pep (40 nmol; TAT-D2 pep [K211-T225]: YGRKKRRQRRRKIYIVLRRRRKRVNT (SEQ ID NO:2)) significantly reversed the disruption of PPI induced by apomorphine in rats while TAT-D2pep-scramb (YGRKKRRQRRRVLRKTRIRRYKIRNV (SEQ ID NO:3) wherein TAT: YGRKKRRQRRR (SEQ ID NO:4)) has no effect on the apomorphine-induced PPI deficit. These effects could not be explained in terms of altered startle reactivity (data not shown). The ability of the TAT-D2pep (administered via ICV) to disrupt the D2-DISC1 interaction was confirmed in co-immunoprecipitation experiments (data not shown).

Example VI

D2R-DISC1 Interaction Site on DISC1

Using an in vitro binding assay, we found that [35S]-DISC1NT probe, but not [35S]-DISC1CT probe, bound with GST-D2IL3-1-1. These data suggest that D2R interacts with the N-terminal of DISC1 directly.

To construct GST-fusion proteins encoding truncated D2l13, cDNA fragments were amplified by PCR with specific primers. All 5' and 3' oligonucleotides incorporated BamH1 site (GGATCC) and Xho1 sites (CTCGAG), respectively, to facilitate subcloning into vector pGEX-4T3 (for GST-fusion protein construction). GST-fusion proteins were prepared from bacterial lysates as described by the manufacturer (Amersham). To confirm appropriate splice fusion and the absence of spurious PCR generated nucleotide errors, all constructs were resequenced. For in vitro binding assays, the probes were made with DISC1-NT or DISC1-CT subcloned into mammalian expression vector pCDNA3 using TNT® T7 Quick Coupled Transcription/Translation System (Promega, Madison, Wis.) and [35S] methionine (PerkinElmer, Waltham, Mass.). Glutathione beads carrying 20 µg GST-fusion proteins of D2IL3 or GST alone were incubated at room temperature for 1 hour with [35S] methionine-labeled CPE probe, respectively. The beads were then washed six times with PBS containing 0.1-0.5% (V/V) Triton X-100 and eluted with 10 mM glutathione elution buffer. Eluates were separated by SDS-PAGE and visualized by autoradiography using BioMax (Kodak) film.

We further mapped the interaction site of D2R-DISC1 on DISC1 by using affinity pull-down techniques. D2R is pulled down by the GST-DISC1-NT-1, but not by other GST-DISC1-NT segments or GST alone in rat striatal tissue.

For affinity pull-down experiments, the solubilized rat striatum extracts (50-100 µg of protein) were incubated with glutathione-Sepharose beads (Pharmacia, Dorval, Quebec, Canada) bound to the indicated GST-fusion proteins of DISC1-NT-1-5 (50 to 100 µg) at 4° C. for 12 hr. Beads were washed three times with 600 µl of PBS containing 0.1-0.5% Triton X-100 before the bound proteins were eluted with glutathione elution buffer. Elutes were incubated in sample buffer and subjected to SDS-PAGE for Western blot analysis. Blots were blocked with 5% nonfat dried milk dissolved in TBST buffer (10 mM Tris, 150 mM NaCl, and 0.1% Tween-20) for 1 hr at room temperature, washed three times with TBST buffer, and then incubated with the anti-D2R antibody (diluted in 1% milk in TBST) overnight at 4° C. and washed again with TBST buffer three times; the membrane was incubated with horseradish peroxidase-conjugated secondary antibody (diluted in 1% milk in TBST) for 1.5 hr at room temperature. The proteins were visualized with enhanced chemiluminescence reagents as described in manufacture's manual (Amersham Biosciences).

Figure 8:
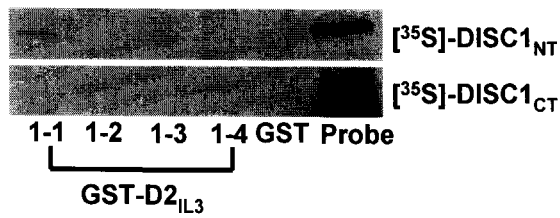
FIGS. 8A-8C show results associated with D2R-DISC1 interaction with DISC1.
Figure 8:
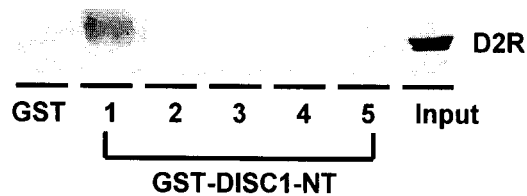
Figure 8:
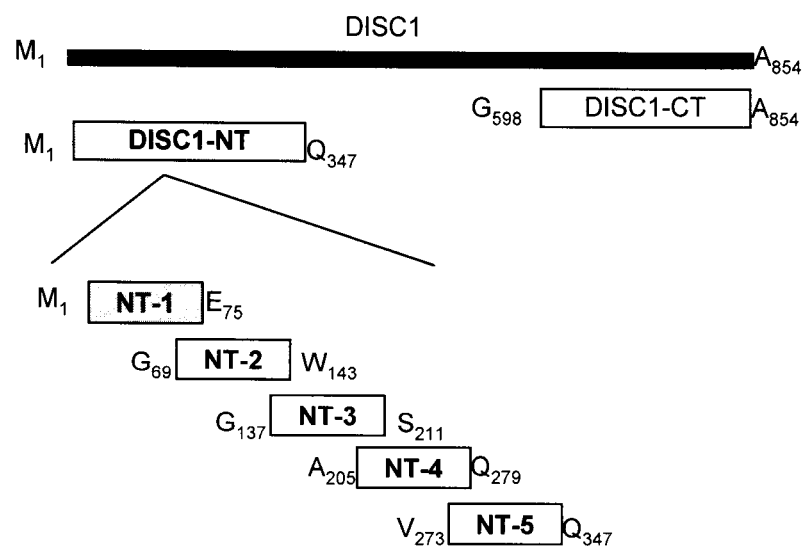

Results obtained are shown in FIG. 8 (A-C). FIG. 8C shows schematic representations of GST-fusion proteins encoding truncated DISC1-NT segments 1-5 as described above.

In some embodiments described herein, the disclosure provides theory and speculation on the mechanism of biological processes. The present invention is not meant to be bound by theory or speculation as to the mechanisms involved in biological processes and the same should not be used to limit the invention in any way.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

1 Murray, C. J. L. and Lopez, A. D., *The Global Burden of Disease*. (Harvard University Press, Boston, 1996).
2 Goeree, R. et al., The economic burden of schizophrenia in Canada in 2004. *Curr Med Res Opin* 21 (12), 2017 (2005).
3 Seeman, P., Targeting the dopamine D2 receptor in schizophrenia. *Expert Opin Ther Targets* 10 (4), 515 (2006); Seeman, P. and Lee, T., Antipsychotic drugs: direct correlation between clinical potency and presynaptic action on dopamine neurons. *Science* 188 (4194), 1217 (1975).
4 Miyamoto, S., Duncan, G. E., Marx, C. E., and Lieberman, J. A., Treatments for schizophrenia: a critical review of pharmacology and mechanisms of action of antipsychotic drugs. *Mol Psychiatry* 10 (1), 79 (2005).
5 Hollerman, J. R., Tremblay, L, and Schultz, W., Influence of reward expectation on behavior-related neuronal activity in primate striatum. *J Neurophysiol* 80 (2), 997 (1998).

6 Iversen, S. D., Interactions between excitatory amino acids and dopamine systems in the forebrain: implications for schizophrenia and Parkinson's disease. *Behav Pharmacol* 6 (5 And 6), 478 (1995).

7 Schultz, W., Dopamine neurons and their role in reward mechanisms. *Curr Opin Neurobiol* 7 (2), 191 (1997).

8 Watanabe, M., Kodama, T., and Hikosaka, K., Increase of extracellulardopamine in primate prefrontal cortex during a working memory task. *J Neurophysiol* 78 (5), 2795 (1997).

9 Beninger, R. J. and Miller, R., Dopamine D1-like receptors and reward-related incentive learning. *Neurosci Biobehav Rev* 22 (2), 335 (1998).

10 Hagan, J. Jr, Middlemiss, D. N., Sharpe, P. C., and Poste, G. H., Parkinson's disease: prospects for improved drug therapy, *Trends Pharmacol Sci* 18 (5), 156 (1997).

11 Missale, C. et al., Dopamine receptors: from structure to function. *Physiol Rev* 78 (1), 189 (1998).

12 Picetti, R. et al., Dopamine D2 receptors in signal transduction and behavior. *Crit Rev Neurobiol* 11 (2-3), 121 (1997).

13 Liu, Y., Hillefors-Berglund, M., and von Euler, G., Modulation of dopamine D3 receptor binding by N-ethylmaleimide and neurotensin. *Brain Res* 643 (1-2), 343 (1994).

14 Schmauss, C., Enhanced cleavage of an atypical intron of dopamine D3-receptor pre-mRNA in chronic schizophrenia. *J Neurosci* 16 (24), 7902 (1996).

15 Van Tol, H. H. et al., Multiple dopamine D4 receptor variants in the human population. *Nature* 358 (6382), 149 (1992), 16 Lichter, J. B. et al., A hypervariable segment in the human dopamine receptor D4 (DRD4) gene. *Hum Mol Genet* 2 (6), 767 (1993).

17 Livak, K. J., Rogers, J., and Lichter, J. B., Variability of dopamine D4 receptor (DRD4) gene sequence within and among nonhuman primate species. *Proc Natl Acad Sci USA* 92 (2), 427 (1995).

18 Sanyal, S. and Van Tol, H. H., Dopamine D4 receptor-mediated inhibition of cyclic adenosine 3',5'-monophosphate production does not affect prolactin regulation. *Endocrinology* 138 (5), 1871 (1997).

19 Seeman, P., Corbett, R., Nam, D., and Van Tol, H. H., Dopamine and serotonin receptors: amino acid sequences, and clinical role in neuroleptic parkinsonism. *Jpn J Pharmacol* 71 (3), 187 (1996).

20. Centonze, D. et al., Dopamine D2 receptor-mediated inhibition of dopaminergic neurons in mice lacking D2L receptors. *Neuropsychopharmacology* 27 (5), 723 (2002).

21 Khan, Z. U. et al., Prominence of the dopamine D2 short isoform in dopaminergic pathways. *Proc Natl Acad Sci USA* 95 (13), 7731 (1998).

22 Lindgren, N. et al., Distinct roles of dopamine D2L and D2S receptor isoforms in the regulation of protein phosphorylation at presynaptic and postsynaptic sites. *Proc Natl Acad Sci USA* 100 (7), 4305 (2003).

23 Montmayeur, J. P. et al., Differential expression of the mouse D2 dopamine receptor isoforms, *FEBS Left* 278 (2), 239 (1991).

24 Usiello, A. et al., Distinct functions of the two isoforms of dopamine D2 receptors. *Nature* 408 (6809), 199 (2000).

25 Wang, Y. et al., Dopamine D2 long receptor-deficient mice display alterations in striatum-dependent functions. *J Neurosci* 20 (22), 8305 (2000).

26 Greengard, P., The neurobiology of slow synaptic transmission, *Science* 294 (5544), 1024 (2001).

27 Beaulieu, J. M. et al., An Akt/beta-arrestin 2/PP2A signaling complex mediates dopaminergic neurotransmission and behavior. *Cell* 122 (2), 261 (2005).

28 Beaulieu, J. M. et al., Lithium antagonizes dopamine-dependent behaviors mediated by an AKT/glycogen synthase kinase 3 signaling cascade. *Proc Natl Acad Sci USA* 101 (14), 5099 (2004)

29 Cross, D. A. et al., Inhibition of glycogen synthase kinase-3 by insulin mediated by protein kinase B. *Nature* 378 (6559), 785 (1995).

30 Gould, T. D., Einat, H., Bhat, R., and Manji, H. K., AR-A014418, a selective GSK-3 inhibitor, produces antidepressant-like effects in the forced swim test. *Int J Neuropsychopharmacol* 7 (4), 387 (2004).

31 Emamian, E. S. et al., Convergent evidence for impaired AKT1-GSK3beta signaling in schizophrenia. *Nat Genet* 36 (2), 131 (2004).

32 Beaulieu, J. M., Sotnikova, T. D., Gainetdinov, R. R., and Caron, M. G., Paradoxical striatal cellular signaling responses to psychostimulants in hyperactive mice. *J Biol Chem* 281 (43), 32072 (2006).

33 Alimohamad, H., Rajakumar, N., Seah, Y. H., and Rushlow, W., Antipsychotics alter the protein expression levels of beta-catenin and GSK-3 in the rat medial prefrontal cortex and striatum. *Biol Psychiatry* 57 (5), 533 (2005).

34 Li, X. et al., Regulation of mouse brain glycogen synthase kinase-3 by atypical antipsychotics. *Int J Neuropsychopharmacol* 10 (1), 7 (2007).

35 Creese, I., Burt, D. R., and Snyder, S. H., Dopamine receptor binding predicts clinical and pharmacological potencies of antischizophrenic drugs. *Science* 192 (4238), 481 (1976).

36 Seeman, P., Lee, T., Chau-Wong, M., and Wong, K., Antipsychotic drug doses and neuroleptic/dopamine receptors. *Nature* 261 (5562), 717 (1976).

37 Seeman, P. and Van Tol, H. H., Dopamine receptor pharmacology. *Trends Pharmacol. Sci* 15 (7), 264 (1994).

38 Crow, T. J. et al., Abnormal involuntary movements in schizophrenia; are they related to the disease process or its treatment? Are they associated with changes in dopamine receptors? *J Clin Psychopharmacol* 2 (5), 336 (1982).

39 Mita, T. et al., Decreased serotonin S2 and increased dopamine D2 receptors in chronic schizophrenics, *Biol Psychiatry* 21 (14), 1407 (1986).

40 Wong, D. F. et al., Quantification of neuroreceptors in the living human brain: IV. Effect of aging and elevations of D2-like receptors in schizophrenia and bipolar illness. *J Cereb Blood Flow Metab* 17 (3), 331 (1997).

41 Wong, D. F. et al., Positron emission tomography reveals elevated D2 dopamine receptors in drug-naive schizophrenics. *Science* 234 (4783), 1558 (1986).

42 Wong, D. F. et al., Quantification of neuroreceptors in the living human brain: III. D2-like dopamine receptors: theory, validation, and changes during normal aging. *J Cereb Blood Flow Metab* 17 (3), 316 (1997).

43 Abi-Dargham, A. et al., Increased baseline occupancy of D2 receptors bydopamine in schizophrenia. *Proc Nat Acad Sci USA* 97 (14), 8104 (2000).

44 Seeman, P, and Kapur, S., Schizophrenia: more dopamine, more D2 receptors. *Proc Natl Acad Sci USA* 97 (14), 7673 (2000).

45 Tailerico, T. et al., Schizophrenia: elevated mRNA for dopamine D2(Longer) receptors in frontal cortex. *Brain Res Mol Brain Res* 7 (2), 160 (2001).

46 Insel, T. R. and Scolnick, E. M., Cure therapeutics and strategic prevention: raising the bar for mental health research. *Mol Psychiatry* 11 (1), 11 (2006).

47 Patil, S. T. et al., Activation of mGlu2/3 receptors as a new approach to treat schizophrenia: a randomized Phase 2 clinical trial. *Nat Med* 13 (9), 1102 (2007).

48 Bartlett, S. E. et al., Dopamine responsiveness is regulated by targeted sorting of D2 receptors. *Proc Natl Acad Sci USA* 102 (32), 11521 (2005).

49 Binda, A. V., Kabbani, N., and Levenson, R., Regulation of dense core vesicle release from PC12 cells by interaction between the D2 dopamine receptor and calcium-dependent activator protein for secretion (CAPS). *Biochem Pharmacol* 69 (10), 1451 (2005).

50 Binda, A. V., Kabbani, N., Lin, R., and Levenson, R., D2 and D3 dopamine receptor cell surface localization mediated by interaction with protein 4.1N. *Mol Pharmacol* 62 (3), 507 (2002).

51 Bofill-Cardona, E. et al., Binding of calmodulin to the D2-dopamine receptor reduces receptor signaling by arresting the G protein activation switch, *J Biol Chem* 275 (42), 32672 (2000).

52 Free, R. B. et al., D1 and D2 dopamine receptor expression is regulated by direct interaction with the chaperone protein calnexin. *J Biol Chem* 282 (29), 21285 (2007).

53 Griffon, N. et al., CLIC6, a member of the intracellular chloride channel family, interacts with dopamine D(2)-like receptors. *Brain Res Mol Brain Res* 117 (1), 47 (2003).

54 Hillion, J. et al., Coaggregation, cointernalization, and codesensitization of adenosine A2A receptors and dopamine D2 receptors. *J Biol Chem* 277 (20), 18091 (2002).

55 Kabbani, N. et al., Interaction with neuronal calcium sensor NCS-1 mediates desensitization of the D2 dopamine receptor. *J Neurosci* 22 (19), 8476 (2002).

56 Lavine, N. et al., G protein-coupled receptors form stable complexes with inwardly rectifying potassium channels and adenylyl cyclase. *J Biol Chem* 277 (48), 46010 (2002).

57 Li, M., Bermak, J. C., Wang, Z. W., and Zhou, Q. Y., Modulation of dopamine D(2) receptor signaling by actin-binding protein (ABP-280). *Mol Pharmacol* 57 (3), 446 (2000).

58 Lin, R. et al., Dopamine D2 and D3 receptors are linked to the actin cytoskeleton via interaction with filamin A. *Proc Nat Acad Sci USA* 98 (9), 5258 (2001).

59 Liu, X. Y. et al., Modulation of D2R-NR2B interactions in response to cocaine. *Neuron* 52 (5), 897 (2006).

60 Macey, T. A., Gurevich, V. V., and Neve, K. A., Preferential Interaction between the dopamine D2 receptor and Arrestin2 in neostriatal neurons. *Mol Pharmacol* 66 (6), 1635 (2004).

61 O'Dowd, B. F. et al., Dopamine receptor oligomerization visualized in living cells. *J Biol Chem* 280 (44), 37225 (2005).

62 Park, S. K. et al., Par-4 links dopamine signaling and depression. *Cell* 122 (2), 275 (2005).

63 Rochoville, M. et al., Receptors for dopamine and somatostatin: formation of hetero-oligomers with enhanced functional activity. *Science* 288 (5463), 154 (2000).

64 Scarselli, M. et al., D2/D3 dopamine receptor heterodimers exhibit unique functional properties. *J Biol Chem* 276 (32), 30308 (2001).

65 Smith, F. D., Oxford, G. S., and Milgram, S. L., Association of the D2 dopamine receptor third cytoplasmic loop with spinophilin, a protein phosphatase-1-interacting protein. *J Biol Chem* 274 (28), 19894 (1999).

66 Takeuchi, Y, and Fukunaga, K., Differential subcellular localization of two dopamine D2 receptor isoforms in transfected NG108-15 cells. *J Neurochem* 85 (4), 1064 (2003).

67 Zou, S. et al., Protein-protein coupling/uncoupling enables dopamine D2 receptor regulation of AMPA receptor-mediated excitotoxicity. *J Neurosci* 25 (17), 4385 (2005).

68 Miller, J. K. et al., Disruption of two novel genes by a translocation co-segregating with schizophrenia. *Hum Mol Genet* 9 (9), 1415 (2000).

69 Blackwood, D. H. et al., Schizophrenia and affective disorders—cosegregation with a translocation at chromosome 1q42 that directly disrupts brain-expressed genes: clinical and P300 findings in a family. *Am J Hum Genet* 69 (2), 428 (2001).

70 Porteous, D. J., Thomson, P., Brandon, N. J., and Millar, J. K., The genetics and biology of DISC1—an emerging role in psychosis and cognition. *Biol Psychiatry* 60 (2), 123 (2006).

71 Ekelund, J. et al., Replication of 1q42 linkage in Finnish schizophrenia pedigrees. *Mol Psychiatry* 9 (11), 1037 (2004).

72 Hwu, H. G. et al., Linkage of schizophrenia with chromosome 1q loci in Taiwanese families. *Mol Psychiatry* 8 (4), 445 (2003), 73 Hamshere, M. L. et al., Genomewide linkage scan in schizoaffective disorder: significant evidence for linkage at 1q42 close to DISC1, and suggestive evidence at 22q11 and 19p13. *Arch Gen Psychiatry* 62 (10), 1081 (2005).

74 Callicott, J. H. et al., Variation in DISC1 affects hippocampal structure and function and increases risk for schizophrenia. *Proc Natl Acad Sci USA* 102 (24), 8627 (2005).

75 Hennah, W, et al., Haplotype transmission analysis provides evidence of association for DISC1 to schizophrenia and suggests sex-dependent effects. *Hum Mol Genet* 12 (23), 3151 (2003).

76 Hodgkinson, C. A. et al., Disrupted in schizophrenia 1 (DISC1): association with schizophrenia, schizoaffective disorder, and bipolar disorder. *Am J Hum Genet* 75 (5), 862 (2004).

77 Sachs, N. A. et al., A frameshift mutation in Disrupted in Schizophrenia 1 in an American family with schizophrenia and schizoaffective disorder. *Mol Psychiatry* 10 (8), 758 (2005).

78 Kockelkorn, T. T. et al., Association study of polymorphisms in the 5' upstream region of human DISC1 gene with schizophrenia. *Neurosci Lett* 368 (1), 41 (2004).

79 Ma, L. et al., Cloning and characterization of DISC1, the mouse ortholog of DISC1 (Disrupted-in-Schizophrenia 1). *Genomics* 80 (6), 662 (2002).

80 Taylor, M. S., Devon, R. S., Millar, J. K., and Porteous, D. J., Evolutionary constraints on the Disrupted in Schizophrenia locus. *Genomics* 81 (1), 67 (2003).

81 Morris, J. A., Kandpal, G., Ma, L., and Austin, C. P., DISC1 (Disrupted-In-Schizophrenia 1) is a centrosome-associated protein that interacts with MAP1A, MIPT3, ATF4/5 and NUDEL: regulation and loss of interaction with mutation. *Hum Mol Genet* 12 (13), 1591 (2003).

82 Ishizuka, K., Paek, M., Kamiya, A., and Sawa, A., A review of Disrupted-In-Schizophrenia-1 (DISC1): neurodevelopment, cognition, and mental conditions. *Biol Psychiatry* 59 (12), 1189 (2006).

83 Millar, J. K. et al., DISC1 and PDE4B are interacting genetic factors in schizophrenia that regulate cAMP signaling. *Science* 310 (5751), 1187 (2005).

84 Kamiya, A. et al., A schizophrenia-associated mutation of DISC1 perturbs cerebral cortex development. *Nat Cell Biol* 7 (12), 1167 (2005).

85 Pletnikov, M. V. et al., PC12 cell model of inducible expression of mutant DISC1: new evidence for a dominant-negative mechanism of abnormal neuronal differentiation. *Neurosci Res* 58 (3), 234 (2007).

86 Koike, H, et al., DISC1 is mutated in the 129S61SvEv strain and modulates working memory in mice. *Proc Nat Acad Sci USA* 103 (10), 3693 (2006).

87 Hikida, T. et al., Dominant-negative DISC1 transgenic mice display schizophrenia-associated phenotypes detected by measures translatable to humans. *Proc Natl Acad Sci USA* 104 (36), 14501 (2007).

88 Li, W. et al., Specific developmental disruption of disrupted-in-schizophrenia-1 function results in schizophrenia-related phenotypes in mice. *Proc Natl Acad Sci USA* 104 (46), 18280 (2007).

89 Pletnikov, M. V. et al., Inducible expression of mutant human DISC1 in mice is associated with brain and behavioral abnormalities reminiscent of schizophrenia. *Mol Psychiatry* 13 (2), 173 (2008).

90 Clapcote, 8. J. et al., Behavioral phenotypes of DISC1 missense mutations in mice. *Neuron* 54 (3), 387 (2007).

91 Lee, F. J. et al., Dopamine transporter cell surface localization facilitated by a direct interaction with the dopamine D2 receptor. *The EMBO journal* 26 (8), 2127 (2007).

92 Lee, F. J. et al., Dual regulation of NMDA receptor functions by direct protein-protein interactions with the dopamine D1 receptor. *Cell* 111 (2), 219 (2002).

93 Liu, F, et al., Direct protein-protein coupling enables cross-talk between dopamine D5 and gamma-50 aminobutyric acid A receptors. *Nature* 403 (6767), 274 (2000).

94 Bergson, C., Levenson, R., Goldman-Rakic, P. S., and Lidow, M. S., Dopamine receptor-interacting proteins: the Ca(2+) connection in dopamine signaling. *Trends Pharmacol Sci* 24 (9), 486 (2003).

95 Okamoto, T. et al., Identification of a Gs activator region of the beta 2-adrenergic receptor that is autoregulated via protein kinase A-dependent phosphorylation. *Cell* 67 (4), 723 (1991).

96 Hebert, T, E, et al., Functional rescue of a constitutively desensitized beta2AR through receptor dimerization. *Biochem J* 330 (Pt 1), 287 (1998);

97 Shupliakov, O. et al., Synaptic vesicle endocytosis impaired by disruption of dynamin-SH3 domain interactions. *Science* 276 (5310), 259 (1997);

98 Lee, F. J., Liu, F., Pristupa, Z. B., and Niznik, H. B., Direct binding and functional coupling of alpha-synuclein to the dopamine transporters accelerate dopamine-induced apoptosis. *Faseb J* 15 (6), 916 (2001).

99 Hattori, T. et al., A novel DISC1-interacting partner DISC1-Binding Zinc-finger protein: implication in the modulation of DISC1-dependent neurite outgrowth. *Mol Psychiatry* 12 (4), 398 (2007).

100 Lieberman, J. A., Kane, J. M., and Alvir, J., Provocative tests with psychostimulant drugs in schizophrenia. *Psychopharmacology* (*Berl*) 91 (4), 415 (1987).

101. Beaulieu, J. M., and Caron, M. G._Akt/GSK3 signaling in the action of psychotropic drugs. *Annu. Rev. Pharmacol. Toxicol* (49), 327 (2009)

102. Beaulieu, J. M. et al., A beta-arrestin 2 signaling complex mediates lithium action on behavior. *Cell.* 132(1), 125 (2008)

103. Beaulieu, J. M., Gainetdinov, R. R., and Caron, M. G. The Akt-GSK-3 signaling cascade in the actions of dopamine. *Trends Pharmacol Sci,* 28(4), 166 (2007)

104. Masri, B. et al., Antagonism of dopamine D2 receptor/beta-arrestin 2 interaction is a common property of clinically effective antipsychotics. *Proc Natl Acad Sci USA* 105 (36), 13656 (2008)

105. Schwarze, S. R., Ho, A., Vocero-Akbani, A., and Dowdy, S. F. (1999). In vivoe protein transduction: delivery of a biologically active protein into the mouse. Science 285, 1569-1572.

106. Aarts, M., Liu, Y., Liu, L., Besshoh, S., Arundine, M., Gurd, J. W., Wang, Y. T., Salter, M. W., and Tymianski, M. (2002). Treatment of ischemic brain damage by perturbing NMDA receptor-PSD-95 protein interactions. Science 298, 846-850.

107. Gabriele, J. P. et al., Decreased expression of a 40-kDa catecholamine-regulated protein in the ventral striatum of schizophrenic brain specimens from the Stanley Foundation Neuropathology Consortium. *Schizophr Res.* 74 (1), 111 (2005)

108. McCullumsmith, R. E. and Meador-Woodruff, J. H. Striatal excitatory amino acid transporter transcript expression in schizophrenia, bipolar disorder, and major depressive disorder. *Neuropsychopharmacology.* 26 (3), 368 (2002)

109. Kapur, S., VanderSpek, S. C., Brownlee, B. A., and Nobrega, J. N. (2003). Antipsychotic dosing in preclinical models is often unrepresentative of the clinical condition: a suggested solution based on in vivo occupancy. J Pharmacol Exp Ther 305, 625-631.

110. Kearn, C. S. et al, Concurrent stimulation of cannabinoid CB1 and dopamine D2 receptors enhances heterodimer formation: a mechanism for receptor cross-talk?, *Mol. Pharmacology* 67, 1697 (2005).

111. Geyer, M. A., K. Krebs-Thomson, et al. (2001). "Pharmacological studies of prepulse inhibition models of sensorimotor gating deficits in schizophrenia: a decade in review."*Psychopharmacology* (*Berl*) 156(2-3): 117-54.

112. Mansbach, R. S., M. A. Geyer, et al. (1988). "Dopaminergic stimulation disrupts sensorimotor gating in the rat." *Psychopharmacology* (*Berl*) 94(4): 507-14.

113 Ralph, R. J. and S. B. Caine (2005). "Dopamine D1 and D2 agonist effects on prepulse inhibition and locomotion: comparison of Sprague-Dawley rats to Swiss-Webster, 129X1/SvJ, C57BLJ6J, and DBA/2J mice." *J Pharmacol Exp Ther* 312(2): 733-41.

What is claimed is:

1. An isolated polypeptide that inhibits dopamine D2 receptor (D2R)—disrupted in schizophrenia-1 interaction, wherein the polypeptide is between 17 and 150 amino acids in length and comprises the sequence of SEQ ID NO: 1.

2. The polypeptide of claim 1 further comprising a protein transduction domain of up to 27 amino acids attached thereto.

3. The polypeptide of claim 1 attached to glutathione-S-transferase, optionally via a spacer molecule.

4. The polypeptide of claim 1 covalently attached to a protein carrier, a non-protein carrier or a solid support.

5. A kit comprising:
   a) the polypeptide of claim 1 and;
   b) a nucleic acid, protein carrier, non-protein carrier, solid support, reagent, solution or any combination thereof.

6. The polypeptide of claim 2, wherein the protein transduction domain is SEQ ID NO:4.

7. The polypeptide of claim 2, wherein the protein transduction domain facilitates transport of the polypeptide across lipid bilayers when attached to the polypeptide as compared to the polypeptide in the absence thereof.

8. An isolated polypeptide consisting of the sequence of SEQ ID NO:1.

9. The isolated polypeptide of claim 1, comprising between 20 and 150 amino acids in length.

10. A method of identifying a polypeptide agent that inhibits the interaction of Dopamine D2 Receptor (D2R) with Disrupted-in-Schizophrenia-1 (DISC1) protein, the method comprising:
   a) testing the polypeptide agent in a cell culture system, said cell culture system comprising cells wherein the D2R associates with DISC1, said testing comprising expressing a nucleic acid in the cells to produce the polypeptide agent comprising the polypeptide of claim 1, and
   b) determining if the polypeptide agent inhibits the interaction of D2R with DISC1.

11. The method of claim 10, wherein said cell culture system comprises co-expression of D2R and DISC1.

12. The method of claim 11, wherein said determining if the polypeptide agent inhibits the interaction of D2R with DISC1 comprises immunoprecipitation.

13. A method of identifying an agent that binds to the polypeptide of claim 1, the method comprising contacting the polypeptide of claim 1 with one or more agents and determining if the one or more agents bind to the polypeptide of claim 1.

14. A method of inhibiting D2R interaction with DISC1 in a mammal comprising administering the polypeptide of claim 1 so it inhibits the interaction of D2R with DISC1 in the mammal.

* * * * *

SEQUENCE LISTING

<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: Human D2R Protein Fragment

<400> SEQUENCE: 1

```
Lys Ile Tyr Ile Val Leu Arg Arg Arg Arg Lys Arg Val Asn Thr
1               5                   10                  15

<210> SEQ ID NO 2
<211> LENGTH: 26
<212> TYPE: PRT
<213> ORGANISM: Artificial Sequence
<220> FEATURE:
<223> OTHER INFORMATION: TAT-[K211-T225]D2R fusion protein

<400> SEQUENCE: 2

Tyr Gly Arg Lys Lys Arg Arg Gln Arg Arg Lys Ile Tyr Ile Val
1               5                   10                  15

Leu Arg Arg Arg Arg Lys Arg Val Asn Thr
            20                  25

<210> SEQ ID NO 3
<211> LENGTH: 26
<212> TYPE: PRT
<213> ORGANISM: Artificial Sequence
<220> FEATURE:
<223> OTHER INFORMATION: TAT-D2 scrambled fusion protein

<400> SEQUENCE: 3

Tyr Gly Arg Lys Lys Arg Arg Gln Arg Arg Val Leu Arg Lys Thr
1               5                   10                  15

Arg Ile Arg Arg Tyr Lys Ile Arg Asn Val
            20                  25

<210> SEQ ID NO 4
<211> LENGTH: 11
<212> TYPE: PRT
<213> ORGANISM: Artificial Sequence
<220> FEATURE:
<223> OTHER INFORMATION: TAT protein sequence

<400> SEQUENCE: 4

Tyr Gly Arg Lys Lys Arg Arg Gln Arg Arg
1               5                   10

<210> SEQ ID NO 5
<211> LENGTH: 75
<212> TYPE: PRT
<213> ORGANISM: Artificial Sequence
<220> FEATURE:
<223> OTHER INFORMATION: N-terminal sequence of human DISC1 protein

<400> SEQUENCE: 5

Met Pro Gly Gly Gly Pro Gln Gly Ala Pro Ala Ala Ala Gly Gly
1               5                   10                  15

Gly Val Ser His Arg Ala Gly Ser Arg Asp Cys Leu Pro Pro Ala Ala
            20                  25                  30

Cys Phe Arg Arg Arg Arg Leu Ala Arg Arg Pro Gly Tyr Met Arg Ser
        35                  40                  45

Ser Thr Gly Pro Gly Ile Gly Phe Leu Ser Pro Ala Val Gly Thr Leu
        50                  55                  60

Phe Arg Phe Pro Gly Gly Val Ser Gly Glu Glu
65                  70                  75

<210> SEQ ID NO 6
<211> LENGTH: 854
<212> TYPE: PRT
<213> ORGANISM: Homo Sapiens
```

<400> SEQUENCE: 6

```
Met Pro Gly Gly Pro Gln Gly Ala Pro Ala Ala Gly Gly
1               5                   10                  15

Gly Val Ser His Arg Ala Gly Ser Arg Asp Cys Leu Pro Ala Ala
            20                  25                  30

Cys Phe Arg Arg Arg Leu Ala Arg Pro Gly Tyr Met Arg Ser
            35                  40                  45

Ser Thr Gly Pro Gly Ile Gly Phe Leu Ser Pro Ala Val Gly Thr Leu
    50                  55                  60

Phe Arg Phe Pro Gly Gly Val Ser Gly Glu Glu Ser His His Ser Glu
65                  70                  75                  80

Ser Arg Ala Arg Gln Cys Gly Leu Asp Ser Arg Gly Leu Leu Val Arg
                85                  90                  95

Ser Pro Val Ser Lys Ser Ala Ala Pro Thr Val Thr Ser Val Arg
                100                 105                 110

Gly Thr Ser Ala His Phe Gly Ile Gln Leu Arg Gly Gly Thr Arg Leu
            115                 120                 125

Pro Asp Arg Leu Ser Trp Pro Cys Gly Pro Gly Ser Ala Gly Trp Gln
    130                 135                 140

Gln Glu Phe Ala Ala Met Asp Ser Ser Glu Thr Leu Asp Ala Ser Trp
145                 150                 155                 160

Glu Ala Ala Cys Ser Asp Gly Ala Arg Arg Val Arg Ala Ala Gly Ser
                165                 170                 175

Leu Pro Ser Ala Glu Leu Ser Ser Asn Ser Cys Ser Pro Gly Cys Gly
            180                 185                 190

Pro Glu Val Pro Pro Thr Pro Pro Gly Ser His Ser Ala Phe Thr Ser
    195                 200                 205

Ser Phe Ser Phe Ile Arg Leu Ser Leu Gly Ser Ala Gly Glu Arg Gly
210                 215                 220

Glu Ala Glu Gly Cys Pro Pro Ser Arg Glu Ala Glu Ser His Cys Gln
225                 230                 235                 240

Ser Pro Gln Glu Met Gly Ala Lys Ala Ala Ser Leu Asp Gly Pro His
                245                 250                 255

Glu Asp Pro Arg Cys Leu Ser Arg Pro Phe Ser Leu Leu Ala Thr Arg
            260                 265                 270

Val Ser Ala Asp Leu Ala Gln Ala Ala Arg Asn Ser Ser Arg Pro Glu
    275                 280                 285

Arg Asp Met His Ser Leu Pro Asp Met Asp Pro Gly Ser Ser Ser Ser
290                 295                 300

Leu Asp Pro Ser Leu Ala Gly Cys Gly Gly Asp Gly Ser Ser Gly Ser
305                 310                 315                 320

Gly Asp Ala His Ser Trp Asp Thr Leu Leu Arg Lys Trp Glu Pro Val
                325                 330                 335

Leu Arg Asp Cys Leu Leu Arg Asn Arg Arg Gln Met Glu Val Ile Ser
            340                 345                 350

Leu Arg Leu Lys Leu Gln Lys Leu Gln Glu Asp Ala Val Glu Asn Asp
    355                 360                 365

Asp Tyr Asp Lys Ala Glu Thr Leu Gln Gln Arg Leu Glu Asp Leu Glu
370                 375                 380

Gln Glu Lys Ile Ser Leu His Phe Gln Leu Pro Ser Arg Gln Pro Ala
385                 390                 395                 400

Leu Ser Ser Phe Leu Gly His Leu Ala Ala Gln Val Gln Ala Ala Leu
                405                 410                 415
```

-continued

```
Arg Arg Gly Ala Thr Gln Gln Ala Ser Gly Asp Asp Thr His Thr Pro
        420                 425                 430
Leu Arg Met Glu Pro Arg Leu Leu Glu Pro Thr Ala Gln Asp Ser Leu
            435                 440                 445
His Val Ser Ile Thr Arg Arg Asp Trp Leu Leu Gln Glu Lys Gln Gln
        450                 455                 460
Leu Gln Lys Glu Ile Glu Ala Leu Gln Ala Arg Met Phe Val Leu Glu
465                 470                 475                 480
Ala Lys Asp Gln Gln Leu Arg Arg Glu Ile Glu Gln Glu Gln Gln
                485                 490                 495
Leu Gln Trp Gln Gly Cys Asp Leu Thr Pro Leu Val Gly Gln Leu Ser
            500                 505                 510
Leu Gly Gln Leu Gln Glu Val Ser Lys Ala Leu Gln Asp Thr Leu Ala
        515                 520                 525
Ser Ala Gly Gln Ile Pro Phe His Ala Glu Pro Pro Glu Thr Ile Arg
    530                 535                 540
Ser Leu Gln Glu Arg Ile Lys Ser Leu Asn Leu Ser Leu Lys Glu Ile
545                 550                 555                 560
Thr Thr Lys Val Cys Met Ser Glu Lys Phe Cys Ser Thr Leu Arg Lys
                565                 570                 575
Lys Val Asn Asp Ile Glu Thr Gln Leu Pro Ala Leu Leu Glu Ala Lys
            580                 585                 590
Met His Ala Ile Ser Gly Asn His Phe Trp Thr Ala Lys Asp Leu Thr
        595                 600                 605
Glu Glu Ile Arg Ser Leu Thr Ser Glu Arg Glu Gly Leu Glu Gly Leu
    610                 615                 620
Leu Ser Lys Leu Leu Val Leu Ser Ser Arg Asn Val Lys Lys Leu Gly
625                 630                 635                 640
Ser Val Lys Glu Asp Tyr Asn Arg Leu Arg Arg Glu Val Glu His Gln
                645                 650                 655
Glu Thr Ala Tyr Glu Thr Ser Val Lys Glu Asn Thr Met Lys Tyr Met
            660                 665                 670
Glu Thr Leu Lys Asn Lys Leu Cys Ser Cys Lys Cys Pro Leu Leu Gly
        675                 680                 685
Lys Val Trp Glu Ala Asp Leu Glu Ala Cys Arg Leu Leu Ile Gln Ser
    690                 695                 700
Leu Gln Leu Gln Glu Ala Arg Gly Ser Leu Ser Val Glu Asp Glu Arg
705                 710                 715                 720
Gln Met Asp Asp Leu Glu Gly Ala Ala Pro Ile Pro Pro Arg Leu
                725                 730                 735
His Ser Glu Asp Lys Arg Lys Thr Pro Leu Lys Val Leu Glu Glu Trp
            740                 745                 750
Lys Thr His Leu Ile Pro Ser Leu His Cys Ala Gly Gly Glu Gln Lys
        755                 760                 765
Glu Glu Ser Tyr Ile Leu Ser Ala Glu Leu Gly Glu Lys Cys Glu Asp
    770                 775                 780
Ile Gly Lys Lys Leu Leu Tyr Leu Glu Asp Gln Leu His Thr Ala Ile
785                 790                 795                 800
His Ser His Asp Glu Asp Leu Ile Gln Ser Leu Arg Arg Glu Leu Gln
                805                 810                 815
Met Val Lys Glu Thr Leu Gln Ala Met Ile Leu Gln Leu Gln Pro Ala
            820                 825                 830
```

```
Lys Glu Ala Gly Glu Arg Glu Ala Ala Ala Ser Cys Met Thr Ala Gly
        835                 840                 845

Val His Glu Ala Gln Ala
    850
```